(12) United States Patent
Okada

(10) Patent No.: US 7,963,910 B2
(45) Date of Patent: Jun. 21, 2011

(54) ENDOSCOPE ACCESSORY, ENDOSCOPE SYSTEM AND METHOD FOR MOUNTING ENDOSCOPE ACCESSORY TO ENDOSCOPE

(75) Inventor: Tsutomu Okada, Tachikawa (JP)

(73) Assignee: Olympus Medical Systems Corporation (JP)

(*) Notice: Subject to any disclaimer, the term of this patent is extended or adjusted under 35 U.S.C. 154(b) by 1067 days.

(21) Appl. No.: 11/471,335

(22) Filed: Jun. 20, 2006

(65) Prior Publication Data

US 2006/0287579 A1    Dec. 21, 2006

(30) Foreign Application Priority Data

Jun. 20, 2005    (JP) .................. 2005-179363

(51) Int. Cl.
*A61B 1/00*    (2006.01)
*A61B 1/12*    (2006.01)
(52) U.S. Cl. ......... 600/104; 600/156; 600/158; 600/153
(58) Field of Classification Search .................. 600/104, 600/106, 114, 153–159; 606/205
See application file for complete search history.

(56) References Cited

U.S. PATENT DOCUMENTS

| | | | | |
|---|---|---|---|---|
| 3,958,566 A * | 5/1976 | Furihata | | 600/159 |
| 5,624,418 A | 4/1997 | Shepard | | 604/319 |
| 5,840,015 A * | 11/1998 | Ogino | | 600/159 |
| 6,068,603 A | 5/2000 | Suzuki | | |
| 2004/0068291 A1* | 4/2004 | Suzuki | | 606/205 |
| 2005/0119522 A1* | 6/2005 | Okada | | 600/106 |

FOREIGN PATENT DOCUMENTS

| | | |
|---|---|---|
| EP | 0 072 689 A2 | 8/1982 |
| JP | 62-74804 | 5/1987 |
| JP | 07-184847 | 7/1995 |
| JP | 08-299255 | 11/1996 |
| JP | 11226024 | 8/1999 |
| JP | 11-309149 | 11/1999 |
| JP | 2005-211453 | 8/2005 |
| WO | WO 2004/075740 | 9/2004 |

OTHER PUBLICATIONS

Letter from German associate dated Sep. 20, 2006 forwarding the Search Report dated Sep. 20, 2006 to Japanese associate, including discussion of relevancy thereof.
Search Report issued by European Patent Office on Sep. 20, 2006 in connection with corresponding European patent application No. EP 06 01 2674.
Japanese Office Action mailed Jan. 4, 2011 in connection with corresponding Japanese Patent Application No. 2005-179363.
English translation of Japanese Office Action issued in connection with corresponding Japanese application provided as an explanation of prior art relevancy.

* cited by examiner

*Primary Examiner* — Thomas J Sweet
*Assistant Examiner* — Ryan Henderson
(74) *Attorney, Agent, or Firm* — Ostrolenk Faber LLP

(57) ABSTRACT

An endoscope accessory, used with an endoscope including a suction conduit communicating with a suction device, an accessory insertion channel, and an operation portion at which entrances of the conduit and channel are formed, includes a tubular insertion unit to be inserted into the channel through the entrance of the channel and to be movable along the channel, and a tubular connection unit provided at a proximal end of the insertion unit and detachably connected to the entrance of the suction conduit. An endoscope system is constituted by combining the accessory with the endoscope. In a method for mounting the accessory onto the endoscope, the insertion unit of the accessory is inserted into the channel through its entrance in the operation portion of the endoscope to be movable along the channel, and the connection unit of the accessory is detachably connected to the entrance of the conduit.

10 Claims, 14 Drawing Sheets

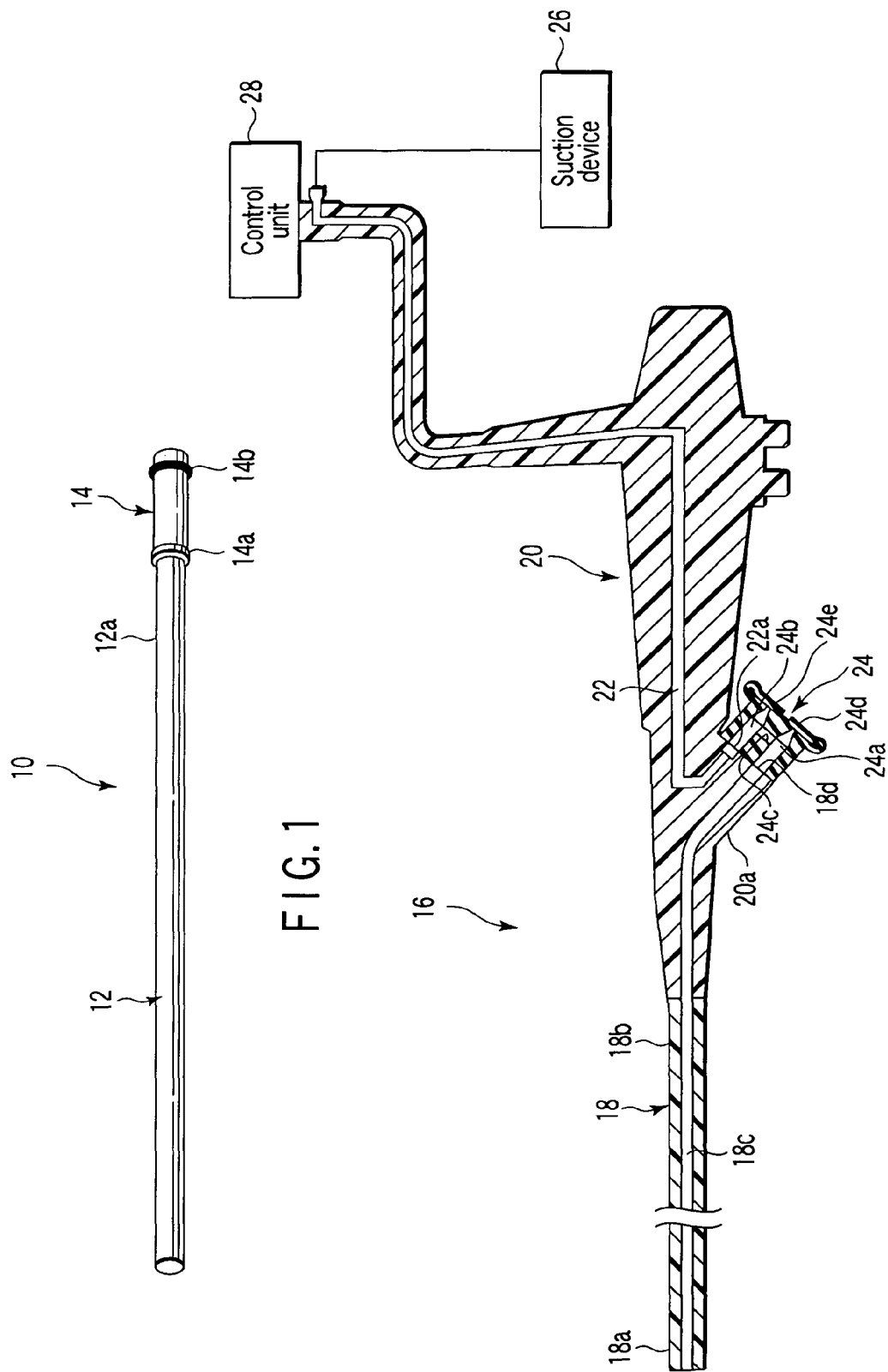

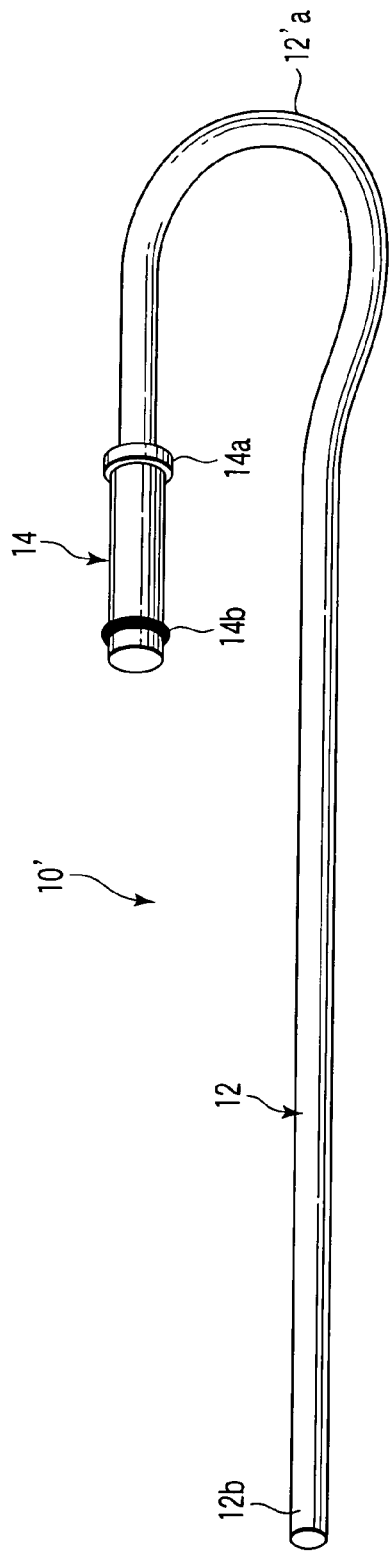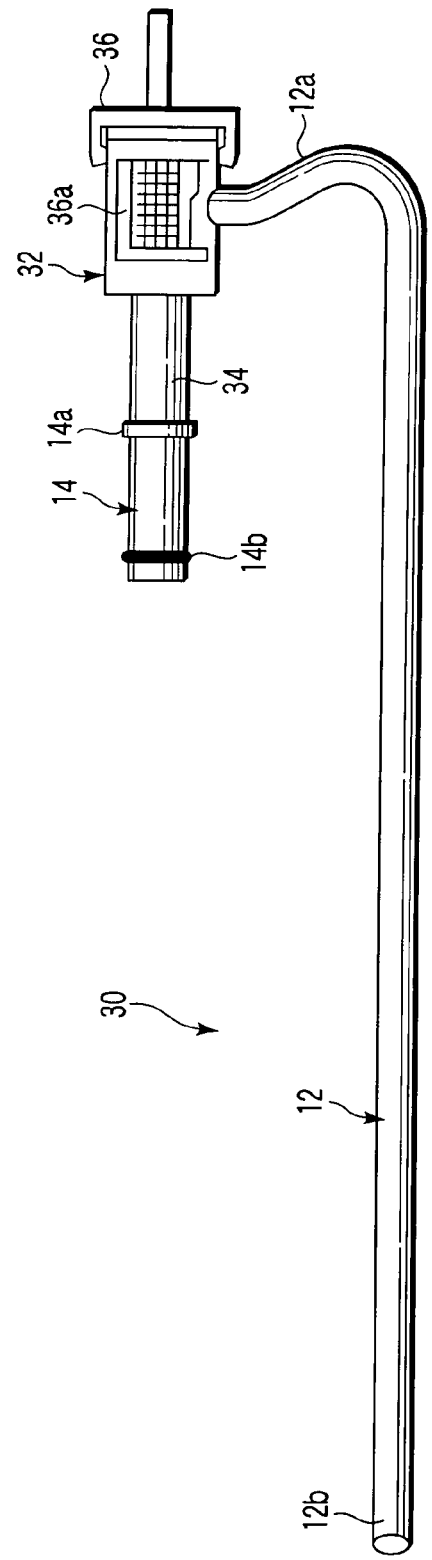

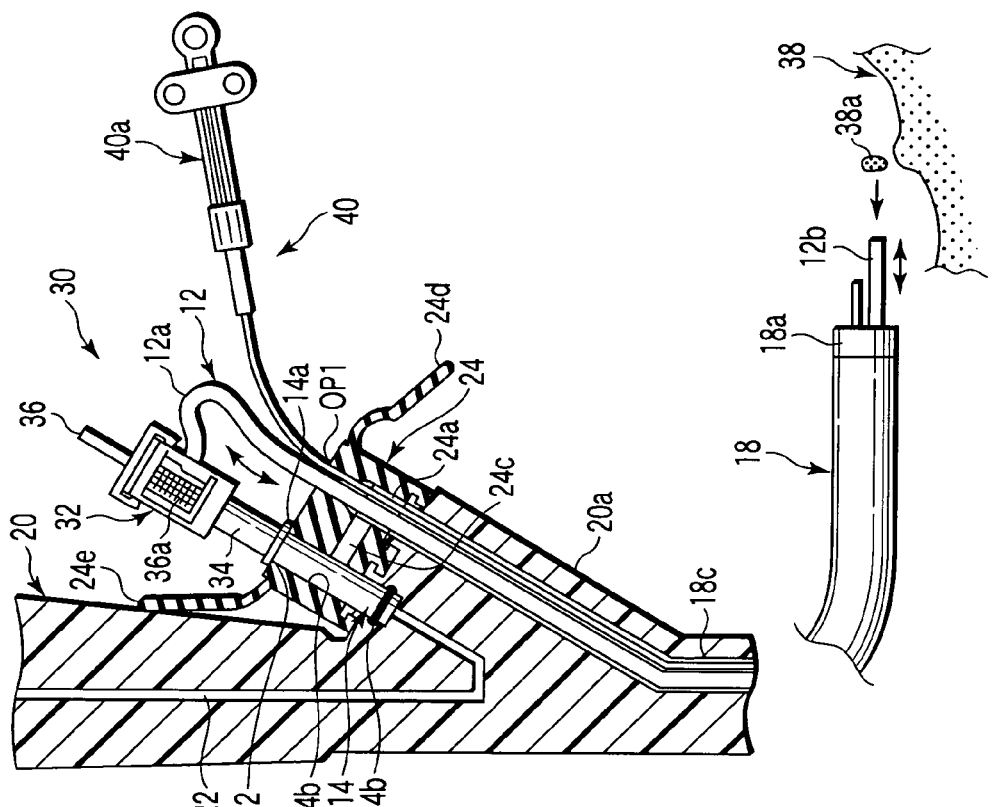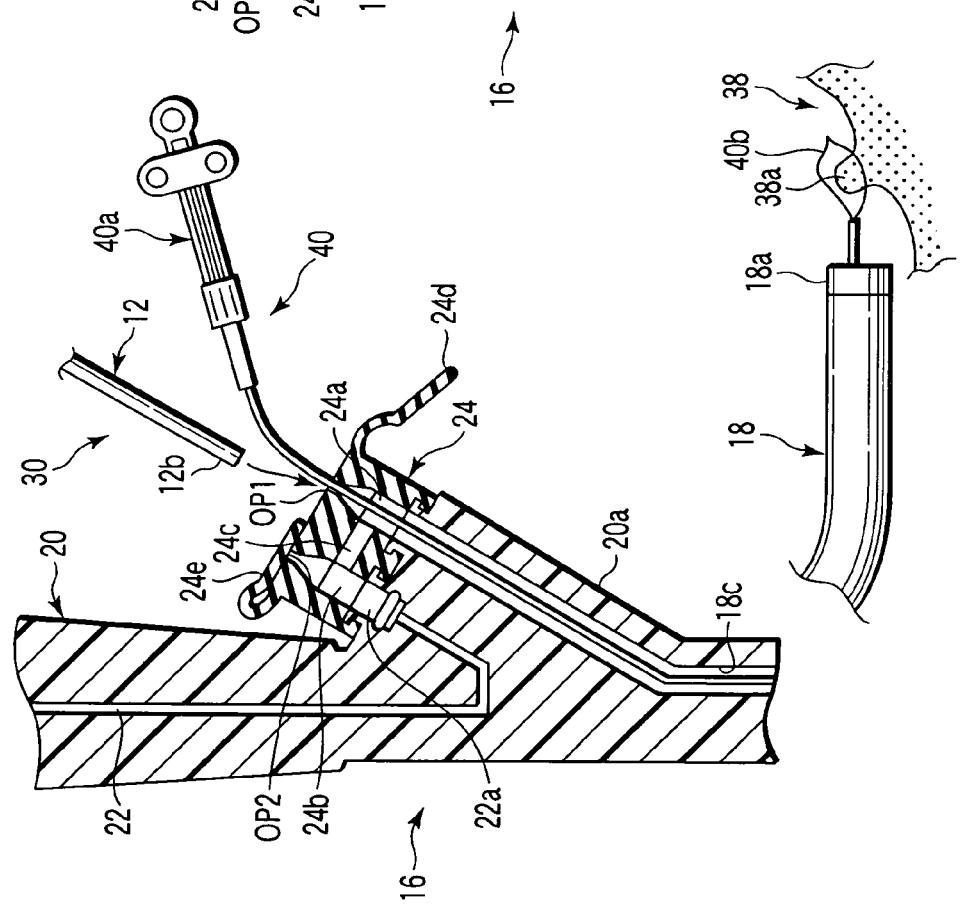
FIG. 8A
FIG. 8B

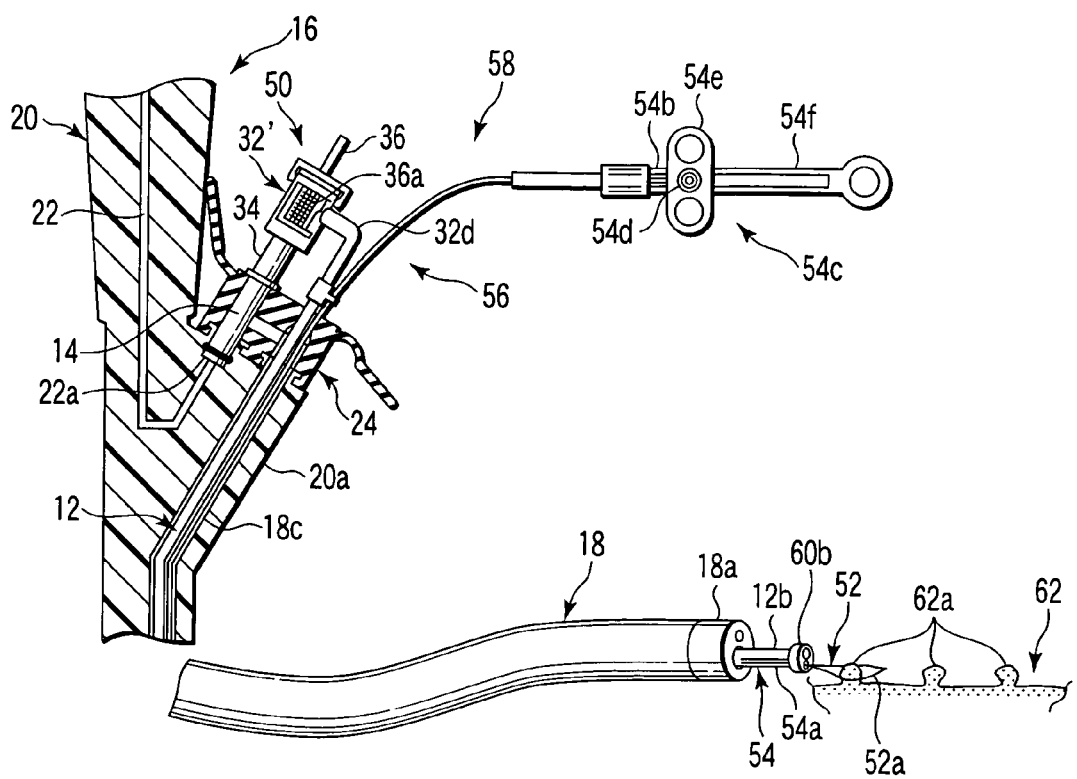
FIG. 12A
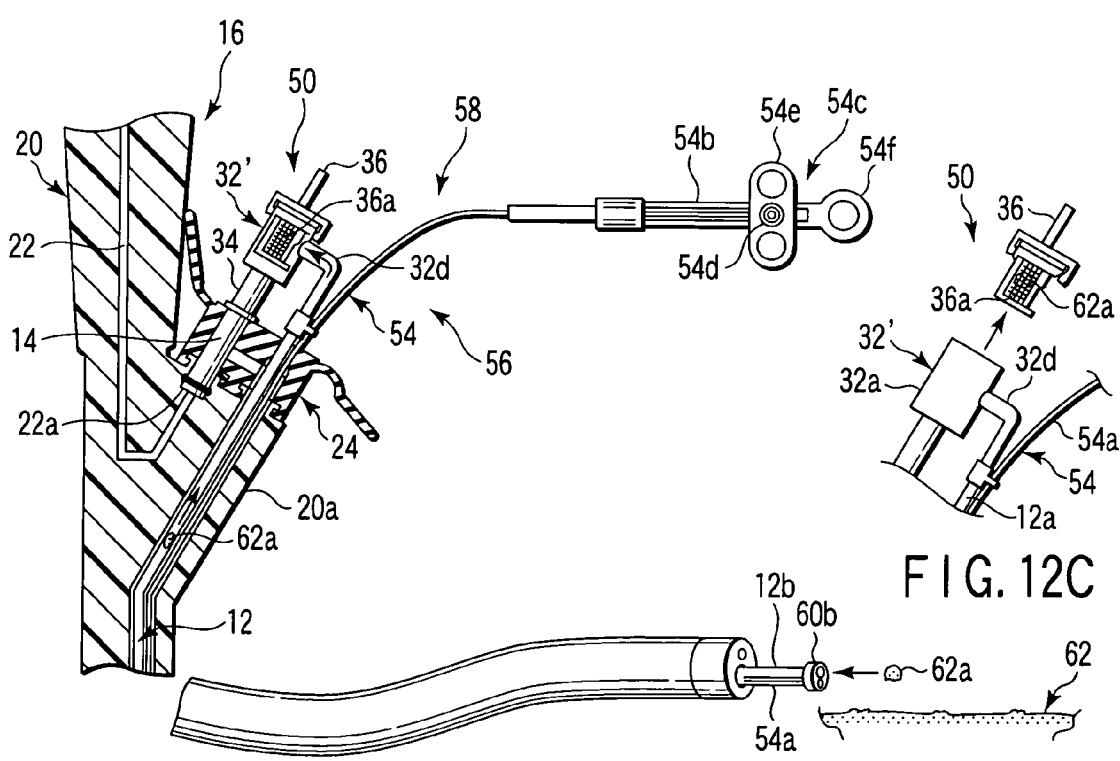
FIG. 12C
FIG. 12B

ENDOSCOPE ACCESSORY, ENDOSCOPE SYSTEM AND METHOD FOR MOUNTING ENDOSCOPE ACCESSORY TO ENDOSCOPE

CROSS-REFERENCE TO RELATED APPLICATIONS

This application is based upon and claims the benefit of priority from prior Japanese Patent Application No. 2005-179363, filed Jun. 20, 2005, the entire contents of which are incorporated herein by reference.

BACKGROUND OF THE INVENTION

1. Field of the Invention

This invention relates to an endoscope accessory, an endoscope system, and a method for mounting an endoscope accessory to an endoscope.

2. Description of the Related Art

When a desired region inside a living organism is observed by using an endoscope, substances such as body fluid and food residues, which hinder observation of the desired region, on the desired region and surrounding regions are sucked via a distal end opening of a suction conduit that is provided in the endoscope and communicates with a suction device.

In a case where a portion of the desired region is collected for examination, the portion of the desired region is cut by using a cutting tool such as a high frequency snare for example, which is provided in the vicinity of the distal end opening of the suction conduit on the endoscope, and then the portion that has been cut is sucked through the distal end opening of the suction conduit, and finally collected by a proximal end collection tool that is provided at an upstream side of the suction device on the suction conduit. Alternatively, the portion of the desired region is collected by a remotely collection tool such as biopsy forceps provided in the vicinity of the distal end opening of the suction conduit on the endoscope.

Japanese Utility Model Application KOKAI Publication No. 62-74804 discloses an endoscope, which comprises: an insertion portion 10; a proximate operation portion 12 including a forceps insertion opening 30, an air and water supply button 26, an eye piece portion 32, etc.; a control unit 16 including a light source, etc.; and a connecting portion 14 for connecting the hand operation portion 12 and the control unit 14 with each other. In the insertion portion 10 of the endoscope, a first suction tube 20A, which extends from a distal end region of the insertion portion 10 to the proximate operation portion 12, is arranged. The first suction tube 20A is connected to a second suction tube 20B via a mesh filter 38 in the proximate operation portion 12, and the second suction tube 20B is connected to a suction device that is not shown.

U.S. Pat. No. 5,624,418 discloses a device 10 for collecting body fluid and tissue fragments from a patient and separating them from each other. The device 10 comprises: a fluid conduit 18 having a distal end region which is disposed at a desired region in a body of the patient; a vacuum conduit 20 having a proximal end region which communicates with a vacuum or suction source not shown; and a tissue collection container 12 which is connected to a proximal end region of the fluid conduit 18 and to a distal end region of the vacuum conduit 20. A first tissue collection basket 30 and a second tissue collection basket 32 are detachably disposed in the tissue collection container 12 along a center line of the container 12, and the first and second tissue collection baskets 30 and 32 can revolve around the center line. The tissue containers 12 can collect tissue pieces, which are sucked together with body fluid from a desired region of a patient's body through the distal end region of the fluid conduit 18, in the first tissue collection basket 30 or the second tissue collection basket 32 by disposing the first tissue collection basket 30 or the second tissue collection basket 32 at a downstream side of the proximal end region of the fluid conduit 18.

FIG. 10 of Japanese Patent Application KOKAI Publication No. 11-226024 discloses an endoscope accessory 1, which comprises an insertion unit 2 to be inserted into an inner hole in an insertion portion of an endoscope not shown and an operation unit 3 connected to a proximal end region of the insertion unit 2. As shown in FIG. 10, a sample collection device 103 is detachably connected to a collection port 107 at a proximal end region of a suction lumen 12 which extends in a sheath 9 of the insertion unit 2 shown in FIG. 11. The sample collection device 103 includes a sample trap 117 which is connected to the collection port 107 with a sample filter 118, and suction means 120 which is connected to the sample trap 117. As shown in FIG. 11, a snare lumen 13 also extends in the sheath 9 of the insertion unit 2, and a snare wire 14 extends in the snare lumen 13. A snare 16 which protrudes from a distal end region of the snare lumen 13 is connected to the snare wire 14 in the front end region of the snare lumen 13.

BRIEF SUMMARY OF THE INVENTION

According to one aspect of the invention, an endoscope accessory used in combination with an endoscope including a suction conduit which communicates with a suction device, an accessory insertion channel into which the accessory is to be inserted, and an operation portion at which an entrance of the suction conduit and an entrance of the accessory insertion channel are formed, comprises: a tubular insertion unit which is configured to be inserted into the accessory insertion channel through the entrance of the accessory insertion channel and to be movable along the accessory insertion channel; and a tubular connection unit which is provided at a proximal end region of the insertion unit and which is configured to be detachably connected to the entrance of the suction conduit.

According to a further aspect of the invention, an endoscope system comprises an endoscope and an endoscope accessory. And, the endoscope includes: an insertion portion which has one end region, the other end region, and an accessory insertion channel extending between the one end region and the other end region, at least one end region being configured to be inserted into a living organism; and an operation portion which is provided at the other end region of the insertion portion and in which a suction conduit communicating with a suction device, an entrance of the suction conduit, and an entrance of the accessory insertion channel are formed. Further, the endoscope accessory includes: a tubular insertion unit which is configured to be inserted into the accessory insertion channel from the entrance of the accessory insertion channel and to be movable along the accessory insertion channel; and a tubular connection unit which is provided at a proximal end region of the insertion unit and which is configured to be detachably connected to the entrance of the suction conduit.

According to a further aspect of the invention, an endoscope system comprises an endoscope and an endoscope accessory. And, the endoscope includes: an insertion portion which has one end region, the other end region, and an accessory insertion channel extending between the one end region and the other end region, at least one end region being configured to be being inserted into a living organism; and an operation portion which is provided at the other end region of the insertion portion, and which has a suction conduit communicating with a suction device, an entrance of the suction conduit, an entrance of the accessory insertion channel, and a communication path allowing the suction conduit and the accessory insertion channel to communicate with each other. Further, the endoscope accessory includes: a tubular insertion unit which is configured to be inserted into the accessory insertion channel from the entrance of the accessory insertion channel and to be movable along the accessory insertion channel: and a tubular connection unit which is provided at a proximal end portion of the insertion unit, and which is configured to be detachably connected to the entrance of the suction conduit and to close the communication between the communication path and the suction conduit.

According to a further aspect of the invention, a method for mounting an endoscope accessory onto an endoscope, comprises: preparing an endoscope including a suction conduit which communicates with a suction device, an accessory insertion channel into which the accessory is to be inserted, and an operation portion in which an entrance of the suction conduit and an entrance of the accessory insertion channel are formed; preparing an endoscope accessory including a tubular insertion unit and a tubular connection unit which is provided at a proximal end region of the insertion unit; inserting the insertion unit of the endoscope accessory into the accessory insertion channel from the entrance of the accessory insertion channel in the operation portion of the endoscope and making the insertion unit being movable along the accessory insertion channel; and connecting the connection unit of the endoscope accessory to the entrance of the suction conduit in the operation portion of the endoscope so as to be detachable.

According to a further aspect of the invention, a method for mounting an endoscope accessory onto an endoscope, comprises: preparing an endoscope including
a suction conduit communicating with a suction device, an accessory insertion channel into which an accessory is to be inserted, and an operation portion in which an entrance of the suction conduit and an entrance of the accessory insertion channel are formed; preparing an endoscope accessory including a tubular insertion unit, a tubular connection unit which is provided at a proximal end region of the insertion unit, and a substance trapping unit which is provided between the insertion unit and the connection unit and which is configured to trap a substance moved in an inner hole of the insertion unit; inserting the insertion unit of the endoscope accessory into the accessory insertion channel from the entrance of the accessory insertion channel in the operation portion of the endoscope and making the insertion unit being movable along the accessory insertion channel; and connecting the connection unit of the endoscope accessory to the entrance of the suction conduit in the operation portion of the endoscope so as to be detachable.

According to a further aspect of the invention, a method for mounting an endoscope accessory onto an endoscope, comprises: preparing an endoscope including an insertion portion which has one end region, the other end region, and an accessory insertion channel extending between the one end region and the other end region, at least one end region being configured to be inserted into a living organism, and an operation portion which is provided at the other end region of the insertion portion, and which has a suction conduit communicating with a suction device, an entrance of the suction conduit, an entrance of the accessory insertion channel, and a communication path allowing the suction conduit and the accessory insertion channel to communicate with each other; preparing an endoscope accessory including a tubular insertion unit and a tubular connection unit which is provided at a proximal end portion of the insertion unit; inserting the insertion unit of the endoscope accessory into the accessory insertion channel from the entrance of the accessory insertion channel in the operation portion of the endoscope and making the insertion unit being movable along the accessory insertion channel; and connecting the connection unit of the endoscope accessory to the entrance of the suction conduit in the operation portion of the endoscope so as to be detachable and closing the communication between the communication path and the suction conduit.

According to a further aspect of the invention, a method for mounting an endoscope accessory onto an endoscope, comprises: preparing an endoscope including an insertion portion which has one end region, the other end region, and an accessory insertion channel extending between the one end region and the other end region, at least one end region being configured to be inserted into a living organism, and an operation portion which is provided at the other end region of the insertion portion, and which has a suction conduit communicating with a suction device, an entrance of the suction conduit, an entrance of the accessory insertion channel, and a communication path allowing the suction conduit and the accessory insertion channel to communicate with each other; preparing an endoscope accessory including a tubular insertion unit, a tubular connection unit which is provided at a proximal end portion of the insertion unit, and a substance trapping unit which is provided between the insertion unit and the connection unit and which is configured to trap a substance moved in an inner hole of the insertion unit; inserting the insertion unit of the endoscope accessory into the accessory insertion channel from the entrance of the accessory insertion channel in the operation portion of the endoscope and making the insertion unit being movable along the accessory insertion channel; and connecting the connection unit of the endoscope accessory to the entrance of the suction conduit in the operation portion of the endoscope so as to be detachable and closing the communication between the communication path and the suction conduit.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE DRAWINGS

The accompanying drawings, which are incorporated in and constitute a part of the invention, illustrate presently embodiments of the invention, and together with the general description given above and the detailed description of the embodiments given below, serve to explain the principles of the invention.

FIG. 1 is a schematic perspective view of a suction catheter according to a first embodiment of an endoscope accessory of the present invention;

FIG. 2 is a schematic longitudinal sectional view of an endoscope which is used in combination with the suction catheter of FIG. 1 to form a first embodiment of an endoscope system of this invention;

FIG. 5 is a schematic perspective view of a modification of the suction catheter of FIG. 1;

FIG. 6 is a schematic perspective view of a suction catheter according to a second embodiment of the endoscope accessory of this invention, wherein the suction catheter comprises an insertion unit, a connection unit and a substance trapping unit between them;

FIG. 8A is an enlarged schematic longitudinal sectional view of the entrance of the accessory insertion channel and the entrance of the suction conduit in the operation portion of the endoscope of FIG. 2, wherein the insertion unit of the suction catheter of FIG. 6 is in a state immediately before the insertion unit is inserted into the entrance of the accessory insertion channel to form a second embodiment of the endoscope system of this invention by combining the suction catheter of FIG. 6 with the endoscope of FIG. 2, and a high frequency snare catheter having a high frequency snare, which is a type of a substance handling unit, is inserted into the accessory insertion channel;

FIG. 8B is a longitudinal sectional view like FIG. 8A, wherein the insertion unit of the suction catheter of FIG. 6 is inserted along with the high frequency snare catheter into the accessory insertion channel of the endoscope of FIG. 2, and the connection unit of the suction catheter is connected to the entrance of the suction conduit in the endoscope of FIG. 2;

FIG. 12A is a schematic view, wherein the one end region of the insertion portion of the endoscope of FIG. 2 is located in the vicinity of a desired region inside a human body, and then a distal end region of the insertion unit of the suction catheter and a distal end region of the high frequency snare catheter, both catheters included in the assembly of FIG. 9 combined with the endoscope, are caused to protrude from the opening of the accessory insertion channel in the one end region of the insertion portion of the endoscope, and then a portion of the desired region inside the human body is cut by the high frequency snare;

FIG. 12B is a schematic view, wherein the portion cut from the desired region inside the human body by the high frequency snare in FIG. 12A is sucked through the distal end region of the insertion unit of the suction catheter of the assembly of FIG. 9;

FIG. 12C is a schematic view, wherein the cut portion sucked through the distal end region of the insertion unit of the suction catheter of the assembly in FIG. 12B is captured in the substance capturing unit of the suction catheter, and then the cut and captured portion is collected from the substance capturing unit;

DETAILED DESCRIPTION OF THE INVENTION

Figure 3B:
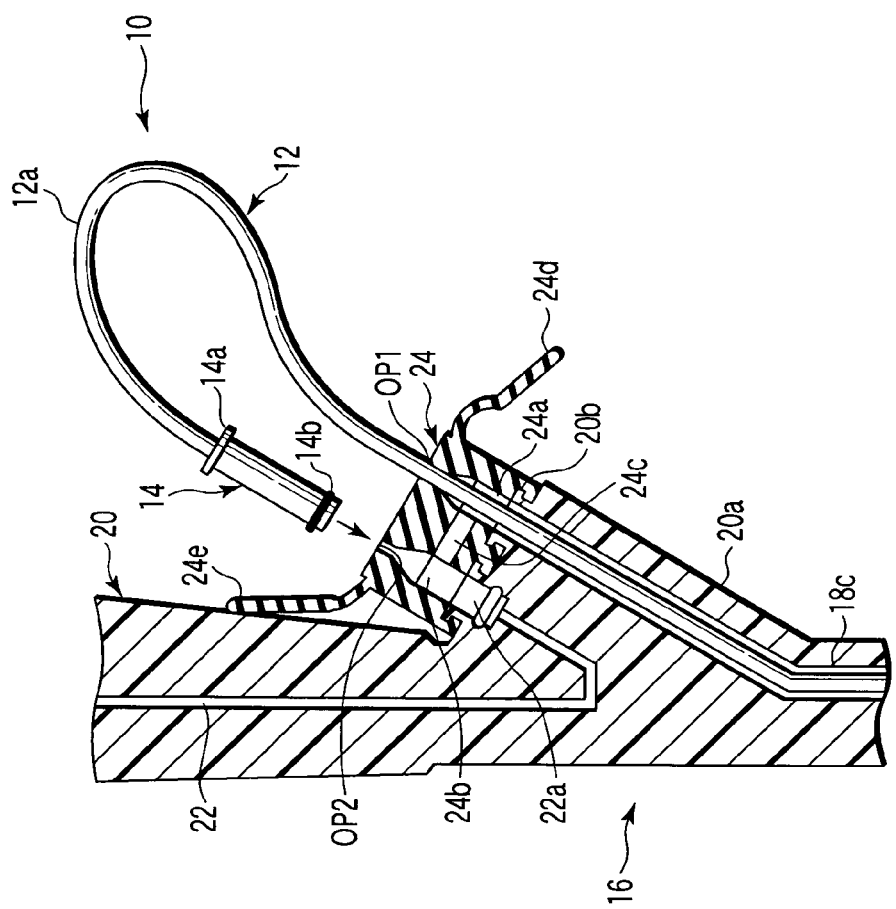
FIG. 3B is a schematic longitudinal section view like FIG. 3A, wherein the insertion unit of the suction catheter of FIG. 1 is inserted into the accessory insertion channel of the endoscope of FIG. 2 and a connection unit of the suction catheter is shown in a state immediately before the connection unit is connected to the entrance of the suction conduit of the endoscope.

In the following, endoscope accessories according to various embodiments and modification of this invention, an endoscope forming various endoscope systems by combination with the above described various endoscope accessories, and various methods for mounting the endoscope accessories to the endoscope are described in detail, with reference to the attached drawings.

First Embodiment

First, a suction catheter 10 according to a first embodiment of an endoscope accessory of this invention, an endoscope 16 which is combined with the suction catheter 10 to constitutes a first embodiment of an endoscope system of this invention, a method for mounting the suction catheter 10 onto the endoscope 16, and an example of a method for using the endoscope system will be described with reference to FIGS. 1 to 4 in the attached drawings.

FIG. 1 schematically shows an exterior of the suction catheter 10 according to the first embodiment of the endoscope accessory of this invention. The suction catheter 10 comprises a tubular insertion unit 12 and a tubular connection unit 14 which is concentrically provided at a proximal end region 12a of the insertion unit 12. The insertion unit 12 is formed of synthetic resin for example and is flexible. The connection unit 14 is formed of synthetic resin for example and is not flexible. A circular outer flange 14a is formed at an inner end region on an outer circumferential surface of the connection unit 14, and a circular sealing unit, such as an O-ring, 14b is disposed at an outer end region on the outer circumferential surface of the connection unit 14.

FIG. 2 shows a schematic longitudinal sectional view of the endoscope 16 which is used in combination with the suction catheter 10 of FIG. 1. The endoscope 16 includes an elongated insertion portion 18 which has one end region 18a and another end region 18b and is flexible, and an operation portion 20 which is provided at the other end region 18b of the insertion portion 18.

The insertion portion 18 has an accessory insertion channel 18c which extends between the one end region 18a and the other end region 18b, and at least one end region 18a is configured to be inserted into a living organism. In addition, various known functional members which are provided in the insertion portion of the conventional endoscope are provided between the one end region 18a and the other end region 18b of the insertion portion 18. Various known functional members include an operation unit which is not shown and can operate to orient the one end region 18a of the flexible insertion portion 18 in a desired direction, an optical system which is not shown and transmits an image in a direction, to which the one end region 18a is oriented, to the other end region 18b, air and water supply channels, etc.

An entrance 18d of the accessory insertion channel 18c and an entrance 22a of a suction conduit 22 are formed in the operation portion 20. The entrance 18d of the accessory insertion channel 18c and the entrance 22a of the suction conduit 22 are disposed so as to be adjacent to each other on a distal end surface of a projection 20a which protrudes from a portion of an outer surface of the operation portion 20. The distal end surface of the projection 20a is covered by a cap member 24 which is detachably provided on the projection 20a.

An insertion opening for the insertion unit 24a, which communicates with the entrance 18d of the accessory insertion channel 18c, an insertion opening for the connection unit 24b, which communicates with the entrance 22a of the suction conduit 22, and a communication path 24c, which communicates with both insertion openings 24a and 24b, are formed in the cap member 24. The cap member 24 also has a first cover 24d which covers the insertion opening for the insertion unit 24a and a second cover 24e which covers the insertion opening for the connection unit 24b.

The cap member 24 of this embodiment is integrally formed with the first cover 24d and the second cover 24e of a material such as rubber which has elasticity.

The suction conduit 22 is formed in the operating portion 20 and is connected to a suction device 26 which is detachably connected to the operation portion 20. The suction device 26 includes a liquid container (not shown), which separates liquid flowing in the suction conduit 22 toward the suction device 26, from the suction conduit 22.

Various known operation devices (not shown) for operating the above described various functional members which are provided in the insertion portion 18 of the conventional endoscope, such as the operation unit (not shown), the optical system (not shown), the air and water supply channels (not shown), etc. are also provided in the operation portion 20. Further, a control unit 28 is detachably connected to the operation portion 20. The control unit 28 supplies the above described various functional members (not shown), which are provided in the insertion portion 18, with electricity, light, and electrical signals required for operating the above described various functional members (not shown), records images obtained by the optical system, and performs various processes on the obtained images.

Figure 3A:
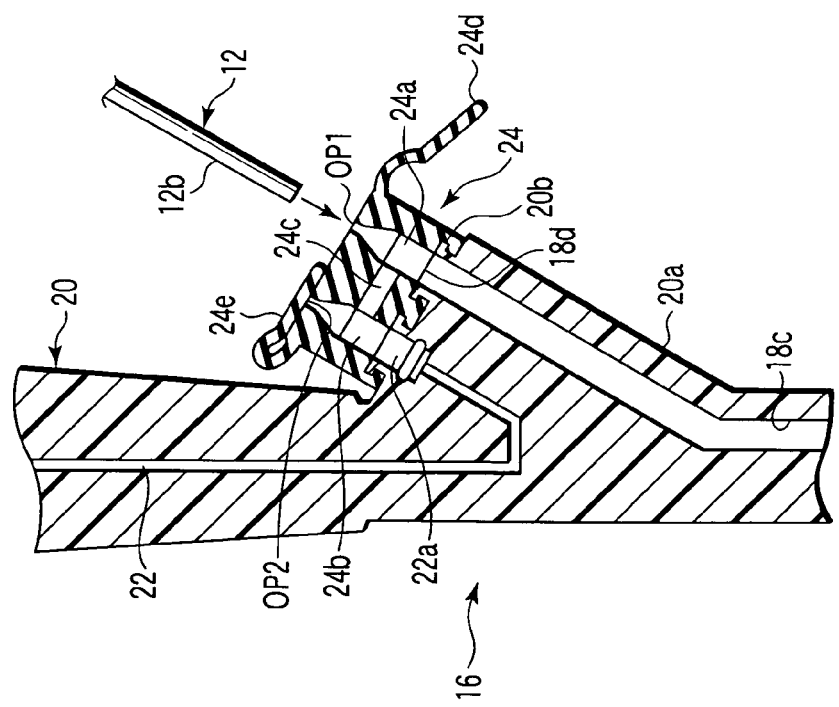
FIG. 3A is an enlarged schematic longitudinal sectional view of an entrance of an accessory insertion channel and an entrance of a suction conduit in an operation portion of the endoscope of FIG. 2, wherein an insertion unit of the suction catheter of FIG. 1 is shown in a state immediately before the suction catheter of FIG. 1 is inserted into the entrance of the accessory insertion channel to be combined with the endoscope of FIG. 2.

FIG. 3A schematically shows a longitudinal sectional view of the projection 20a and the vicinity thereof in the operation portion 20 of the endoscope 16 in an enlarged scale. FIG. 3A shows that a circular groove is formed in an inner circumferential surface of an indent formed in a base end portion of the base member 24 to surround the insertion opening for the insertion unit 24a and the insertion opening for the connection unit 24b, and the circular groove of the base member 24 is fitted on a circular protrusion 20b formed on a distal end region of an outer surface of the projection 20a. As a result of this fitting, the cap member 24 is detachably connected to the projection 20a in a sealed state. Furthermore, FIG. 3A shows that each of the insertion opening for the insertion unit 24a and insertion opening for the connection unit 24b becomes gradually narrow as each of the insertion openings approaches to a projecting end surface of a projecting end region of the base member 24.

The length of the insertion unit 12 of the suction catheter 10 is set to be longer than the sum of the length of the accessory insertion channel 18c from the end surface of the one end region 18a of the insertion portion 18 of the endoscope 16 to the distal end surface of the projection 20a of the operation portion 20 and the length of the insertion opening for the insertion unit 24a of the cap member 24 provided on the projection 20a. In addition, the outer diameter of the suction catheter 10 is smaller than each of the inner diameter of the accessory insertion channel 18c and the inner diameter of the insertion opening for the insertion unit 24a, but larger than a narrowed point OP1 of the insertion opening for the insertion unit 24a in the projecting end surface of the base 24.

Furthermore, the outer diameter of the connection unit 14 of the suction catheter 10 is set to be substantially the same as each of the inner diameter of the entrance 22a of the suction conduit 22 and the inner diameter of the insertion opening for the connection unit entry 24b, excluding the outer flange 14a and the sealing unit 14b on both longitudinal end regions of the connection unit 14, but larger than the narrowed point OP2 of the insertion opening for the connection unit 24b in the projecting end surface of the base 24.

Next, a method for mounting the suction catheter 10 to the endoscope 16 will be described with reference to FIGS. 3A and 3B. By this mounting, the suction catheter 10, which is configured as described above and is a type of endoscope accessory, is combined with the endoscope 16, which is configured as described above, to constitute the endoscope system according to the first embodiment of this invention.

First, as shown in FIG. 3A, the first cover 24d of the cap member 24 is opened to expose the narrowed point OP1 of the insertion opening for the insertion unit 24a, and then the distal end region 12b of the insertion unit 12 of the suction catheter 10 is inserted into the narrowed point OP1. The insertion unit 12 is sent into the accessory insertion channel 18c through the narrowed point OP1 of the insertion opening for the insertion unit 24a of the cap member 24 until the end surface (insertion end) of the distal end region 12b of the insertion unit 12 reaches the vicinity of the opening of the accessory insertion channel 18c in the end surface of the one end region 18a of the insertion portion 18 of the endoscope 16. Meanwhile, the insertion unit 12 seals the narrowed point OP1.

Next, as shown in FIG. 3B, the second cover 24e of the cap member 24 is opened to expose the narrowed point OP2 of the insertion opening for the connection unit 24b, and then the outer end region (insertion end region) of the connection unit 14 of the suction catheter 10 is inserted into the narrowed point OP2. The connection unit 14 is sent into the insertion opening for the connection unit 24b through the narrowed point OP2 of the insertion opening for the connection unit 24b of the cap member 24 until the sealing unit 14b of the outer end region (insertion end region) of the connection unit 14 detachably engages with a circular groove formed in the entrance 22a of the suction conduit 22. Meanwhile, the connection unit 14 seals the narrowed point OP2, and the outer flange 14a of the inner end region of the connection unit 14 is disposed at the outside of the narrowed point OP2. Further, the connection unit 14 closes the communication between the insertion opening for the insertion unit 24a and the insertion opening for the connection unit 24b by the communication path 24c in the cap member 24, that is the communication between the accessory insertion channel 18c and the suction conduit 22 is closed.

Figure 4:
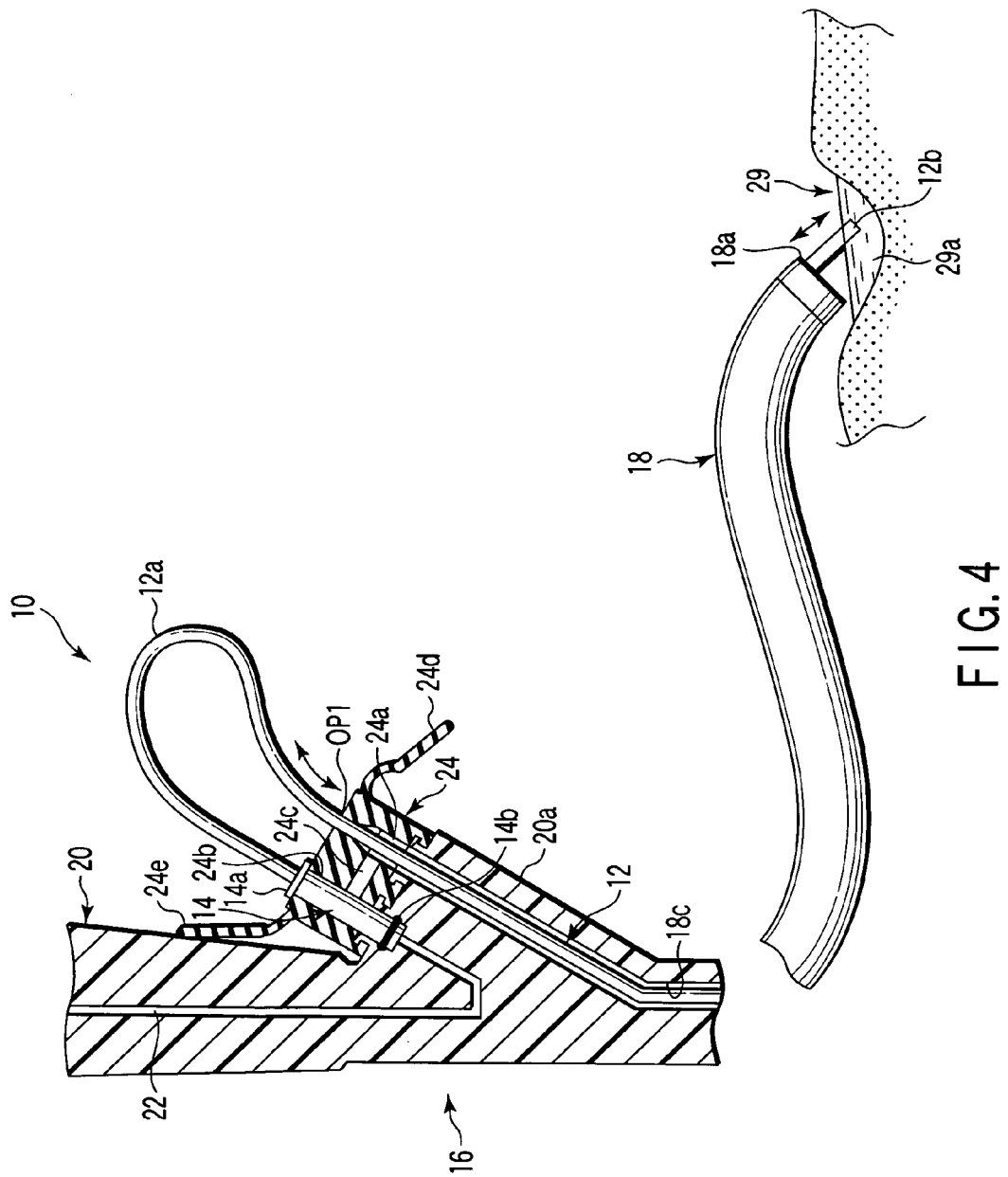
FIG. 4 is a schematic view, wherein one end region of an insertion portion of the endoscope of FIG. 2 is located in the vicinity of a desired region inside a human body, and then the one end region of the insertion unit of the suction catheter of FIG. 1 combined with the endoscope is caused to protrude from an opening of the accessory insertion channel in the one end region of the insertion portion of the endoscope, and then body fluid in the desired region inside the human body is sucked by the one end region of the insertion unit of the suction catheter.

Next, with reference to FIG. 4, an operation for collecting a substance (for example, body fluid, other fluid or food residues) from a desired region inside a living organism (such as a human) will be described as an example of the method for using the endoscope system according to the first embodiment configured as described above.

First, the one end region 18a of the insertion portion 18 of the endoscope 16 in which the suction catheter 10 is not mounted is inserted into the living organism (such as human) until the one end region 18a of the insertion portion 18 reaches a position near to the desired region 29 inside the living organism (such as human). During this time, an operator of the endoscope 16 can view an image in a direction, in which the end surface of the one end region 18a is directed, by the end portion of the abovementioned optical system in the end surface of the one end region 18a.

Next, the suction catheter 10 is combined with the endoscope 16 as described above with reference to FIGS. 3A and 3B. And, the operator operates the proximal end region 12a of the insertion unit 12 of the suction catheter 10, which is exposed in the outside of the cap member 24 of the projection 20a of the operation portion 20 of the endoscope 16. With this operation, the insertion unit 12 is moved along the center line of accessory insertion channel 18c of the insertion portion 18 of the endoscope 16 to protrude the distal end region 12b of the insertion unit 12 from the opening of the accessory insertion channel 18c in the end surface of the one end region 18a of the insertion portion 18 of the endoscope 16 as shown in FIG. 4, and the distal end region 12b of the insertion unit 12 is entered into the substance (such as body fluid, other fluid or food residues) 29a at the desired region 29 inside the living organism (such as a human). Next, the suction device 26 of the endoscope 16 is operated so that the substance can be sucked into the inner hole of the insertion unit 12 from the distal end region 12b of the insertion unit 12. The substance sucked into the inner hole of the insertion unit 12 is further sucked into the suction conduit 22 of the endoscope 16 via the connection unit 14 of the proximal end region 12a of the insertion unit 12, and then is collected in the aforementioned liquid container (not shown) of the suction device 26.

In such a collecting operation, there is no need to move the end surface of the one end region 18a of the insertion portion 18 of the endoscope 16 while the end surface of the one end region 18a is oriented toward the desired region 29 inside the living organism (such as human body). Therefore, the view field of the image that the operator views by the aforementioned optical system of the endoscope 16 does not change, and the end portion of the aforementioned optical system in the end surface of the one end region 18a of the insertion portion 18 of the endoscope 16 does not being dirtied by the substance (such as body fluid, other fluid or food residues) 29a at the desired region 29 inside the living organism (such as a human) so that the image keeps clear. As a result, the collecting operation can be performed simply.

In this embodiment, the connection unit 14 and the sealing unit 14a in the suction catheter 10 are independent from each other, but according to the aspect of this invention, the sealing unit 14a and the connection unit 14 may be integrally formed of the same member.

Furthermore, in this embodiment, the insertion unit 12, the connection unit 14, and the sealing unit 14a are independent from each other, but according to the aspect of this invention, the insertion unit 12, the connection unit 14, and the sealing unit 14a may be integrally formed of the same member.

[Modification]

FIG. 5 schematically shows a perspective view of a modification of the suction catheter 10 shown in FIG. 1. Most part of components of a suction catheter 10' of the modification shown in FIG. 5 is the same as that of the suction catheter 10 shown in FIG. 1. Thus, the components of the suction catheter 10' of the modification in FIG. 5 which are the same as the components of the suction catheter 10 are designated by the same reference numerals used to designate the components of the suction catheter 10 in FIG. 1 corresponding to those of the suction catheter 10', and the detailed descriptions thereof will be omitted.

The difference between the suction catheter 10' of the modification in FIG. 5 and the suction catheter 10 in FIG. 1 is the structure of a proximal end region 12'a of the insertion unit 12. The proximal end region 12'a of the insertion unit 12 of the suction catheter 10' in FIG. 5 is deformed in advance so as to have an U-shape.

During the combining operation of the suction catheter 10 in FIG. 1 with the endoscope 16 in FIG. 2, the proximal end region 12a of the insertion unit 12 of the suction catheter 10 in FIG. 1 needs to be bent in a U-shape. However, there is no need for the operation of bending the proximal end region 12a of the insertion unit 12 of the suction catheter 10' in FIG. 5 in a U-shape during the combining operation of the suction catheter 10' in FIG. 5 with the endoscope 16 in FIG. 2. Thus, the combining operation of the suction catheter 10' in FIG. 5 with the endoscope 16 in FIG. 2 is easier than the combining operation of the suction catheter 10 in FIG. 1 with the endoscope 16 of FIG. 2.

Second Embodiment

Next, a suction catheter 30 according to a second embodiment of the endoscope accessory of this invention, a method for mounting the suction catheter 30 onto the endoscope 16 to constitute a second embodiment of the endoscope system of this invention, and an example of a method for using the endoscope system will be described with reference to FIGS. 6 to 8B in the attached drawings.

Figure 7:
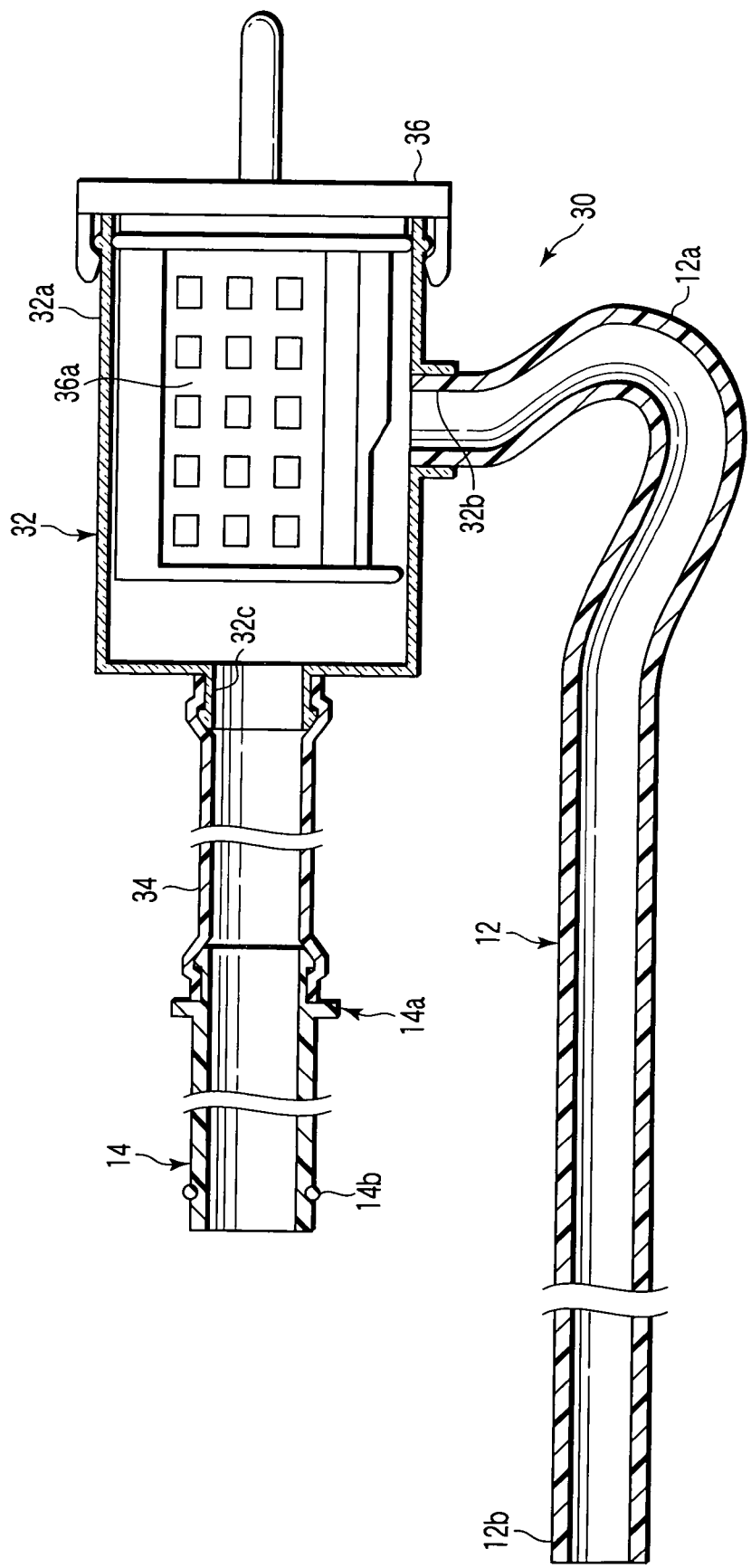
FIG. 7 is an enlarged schematic longitudinal sectional of the suction catheter of FIG. 6.

FIG. 6 schematically shows a perspective view of the suction catheter 30 according to the second embodiment of the endoscope accessory of this invention, and FIG. 7 schematically shows a longitudinal sectional view of the suction catheter 30 of FIG. 6 in an enlarged scale.

Most part of components of the suction catheter 30 of the second embodiment is the same as that of the suction catheter 10 shown in FIG. 1. Thus, the components of the suction catheter 30 of the second embodiment which are the same as the components of the suction catheter 10 in FIG. 1 are designated by the same reference numerals used to designate the components of the suction catheter 10 in FIG. 1 corresponding to those of the suction catheter 30, and the detailed descriptions thereof will be omitted.

The difference between the suction catheter 30 of the second embodiment and the suction catheter 10 in FIG. 1 is that a substance trapping unit 32 which is configured to trap a substance sucked through the inner hole of the insertion unit 12 from the distal end region 12b of the insertion unit 12 is provided between the insertion unit 12 and the connection unit 14.

The substance trapping unit 32 includes a transparent cylindrical container 32a having one open end. An entrance opening 32b, to which the proximal end region 12a of the insertion unit 12 is connected, is formed in the outer peripheral surface of the container 32a, and an exit opening 32c, to which a flexible tubular connection member 34 is connected, is formed on the closed other end surface of the container 32a. The connection member 34 is connected to the inner end region of the connection unit 14.

A cover 36 is detachably attached to the one end opening of the container 32a, and the cover 36 seals the one end opening when the cover 36 is attached to the one end opening of the container 32a. The cover 36 includes a net-like trap member 36a which partitions the inner space of the container 32a into an entrance compartment communicated with the entrance opening 32b and an exit compartment communicated with the exit opening 32c.

Next, a method for mounting the suction catheter 30 to the endoscope 16 will be described with reference to FIGS. 8A and 8B. By this mounting, the suction catheter 30, which is configured as described above and is a type of endoscope accessory, is combined with the endoscope 16, which is configured as described above, to constitute the endoscope system according to the second embodiment of this invention. Further, an operation for collecting a substance (for example, tissue fragment) of a desired region inside a living organism (such as a human) will be described as an example of the method for using the endoscope system according to the second embodiment configured as described above.

The one end region 18a of the insertion portion 18 of the endoscope 16, in the accessory insertion channel 18c of which nothing has been inserted, is inserted into the living organism (such as a human) until the one end region 18a of the insertion portion 18 reaches a position near to the desired region 38 inside the living organism (such as human). During this time, an operator of the endoscope 16 can view an image in a direction, in which the end surface of the one end region 18a is directed, by the end portion of the abovementioned optical system in the end surface of the one end region 18a.

Next, as shown in FIG. 8A, the first cover 24d of the cap member 24 is opened to expose the narrowed point OP1 of the insertion opening for the insertion unit 24a, and a known high frequency snare catheter 40 which is a type of endoscope accessory is inserted into the narrowed point OP1. In addition, by operating a high frequency snare operation device 40a of the high frequency snare catheter 40, which is exposed in the outside of the cap member 24 of the projection 20a of the operation portion 20 of the endoscope 16, a high frequency snare 40b at a distal end of the high frequency snare catheter 40 is projected toward the desired region 38 inside the living organism (such as a human) from the opening of the accessory insertion channel 18c in the end surface of the one end region 18a, and then the high frequency snare 40b is used to cut out a portion (tissue fragment) 38a of the desired region 38.

Next, the distal end region (that is the insertion end region) 12b of the insertion unit 12 of the suction catheter 30 is inserted into the narrowed point OP1 of the insertion opening for the insertion unit 24a, and then the insertion unit 12 is sent into the accessory insertion channel 18c until the distal end surface of the distal end region 12b reaches the vicinity of the opening of the accessory insertion channel 18c in the end surface of the one end region 18a of the insertion portion 18 of the endoscope 16. During this time, the insertion unit 12 together with the high frequency snare catheter 40 seals the narrowed point OP1.

Next, as shown in FIG. 8B, the second cover 24e of the cap member 24 is opened to expose the narrowed point OP2 of the insertion opening for the connection unit 24b, and then the outer end of the connection unit 14 of the suction catheter 30 is inserted into the narrowed point OP2 until the sealing unit 14 on the outer end region (that is the insertion end region) of the connection unit 14 is detachably engaged with the circular groove in the entrance 22a of the suction conduit 22. During this time, the connection unit 14 seals the narrowed point OP2, and closes the communication between the insertion opening for the insertion unit 24a and the insertion opening for the connection unit 24b to close the communication between the accessory insertion channel 18c and the suction conduit 22.

Next, the operator operates the proximal end region 12a of the insertion unit 12 of the suction catheter 30, which is exposed in the outside of the cap member 24 of the projection 20a of the operation portion 20 of the endoscope 16. With this operation, the insertion unit 12 is moved along the center line of accessory insertion channel 18c of the insertion portion 18 of the endoscope 16 to protrude the distal end region 12b of the insertion unit 12 from the opening of the accessory insertion channel 18c in the end surface of the one end region 18a of the insertion portion 18 of the endoscope 16 as shown in FIG. 8B, and the distal end region 12b of the insertion unit 12 is located near to the portion (tissue fragment) 38a of the desired region 38, which is cut out from the desired region 38 inside the living organism (such as a human) by the high frequency snare catheter 40. Next, the suction device 26 of the endoscope 16 is operated so that the portion (tissue fragment) 38a can be sucked into the inner hole of the insertion unit 12 from the distal end region 12b of the insertion unit 12. The portion (tissue fragment) 38a sucked into the inner hole of the insertion unit 12 is entered from the entrance opening 32b in the container 32a of the substance trapping unit 32, and is trapped by the trap member 36a.

The portion (tissue fragment) 38a trapped by the trap member 36a can be collected from the trap member 36a by removing the trap member 36a together with the cover 36 from the container 32a after the operation of the suction device 26 of the endoscope 16 is stopped.

If there is a substance (such as body fluid, other fluid or food residues) which is sucked together with the portion (tissue fragment) 38a into the inner hole of the insertion unit 12 from the desired region 38 inside the living organism (such as a human), the substance which passes through the trap member 36a in the container 32a of the substance trapping unit 32 is further sucked into the suction conduit 22 of the endoscope 16 via the connection unit 14 connected to the exit opening 32c by the connection member 34, and then is collected in the aforementioned liquid container (not shown) of the suction device 26.

The suction catheter 30 of this embodiment and the endoscope system including the suction catheter 30 can obtain the same advantages as those obtained by the suction catheter 10 of FIG. 1 and by the endoscope system including the suction catheter 10. In addition, the operator of the endoscope 16 can easily recognize that the portion 38a of the desired region 38, which is a type of substance collected from the desired region 38 inside the living organism (such as human), is surely collected in the container 32a of the substance trapping unit 32 which is close to the operation portion 20 of the endoscope 16.

In the endoscope unit, which is according to the first embodiment and which uses the suction catheter 10 according to the first embodiment and which is described above with reference to FIG. 4, the substance sucked by the suction catheter 10 from the desired region 29 inside the living organism (such as human) is not only sucked in the insertion unit 12 of the suction catheter 10, but also sucked in the suction conduit 22 of the endoscope 16 through the connection unit 14 of the proximal end region 12a of the insertion unit 12 of the suction catheter 10, and the sucked substance is finally collected in the aforementioned liquid container (not shown) of the suction device 26. In this embodiment, since the sucked substance must be moved for a long distance from the desired region 29 inside the living organism (such as a human) to the aforementioned liquid container (not shown), there is a large possibility that the sucked substance is damaged.

However, in the endoscope unit of the second embodiment which uses the suction catheter 30 of the second embodiment and which is described above with reference to FIGS. 6 to 8B, the portion 38a of the desired region 38, which is a type of substance and which is sucked by the suction catheter 30 from the desired region 38 inside the living organism (such as a human), is trapped in the trap member 36a of the substance trapping unit 32 only after the portion 38a is passed through the suction catheter 30. Therefore, since the moving distance of the sucked portion 38a from the desired region 38 inside the living organism (such as a human) to the substance trapping unit 32 is short, there is a little possibility that the sucked substance is damaged.

In the endoscope unit of the second embodiment which uses the suction catheter 30 of the second embodiment and which is described above with reference to FIGS. 6 to 8B, the endoscope accessory which is inserted together with the suction catheter 30 into the accessory insertion channel 18c of the insertion portion 18 of the endoscope 16, is the well known high frequency snare catheter 40. However, according to the aspect of this invention, various well known endoscope accessory excluding the high frequency snare catheter 40 may be inserted together with the suction catheter 30 into the accessory insertion channel 18c of the insertion portion 18 of the endoscope 16 and may be used together with the suction catheter 30.

Third Embodiment

Next, an assembly 58 of a suction catheter 50 and a high frequency snare catheter 56, according to a third embodiment of the endoscope accessory of this invention, a method for mounting the assembly 58 onto the endoscope 16 to constitute a third embodiment of the endoscope system of this invention, and an example of a method for using the endoscope system will be described with reference to FIGS. 9 to 12B in the attached drawings.

Figure 9:
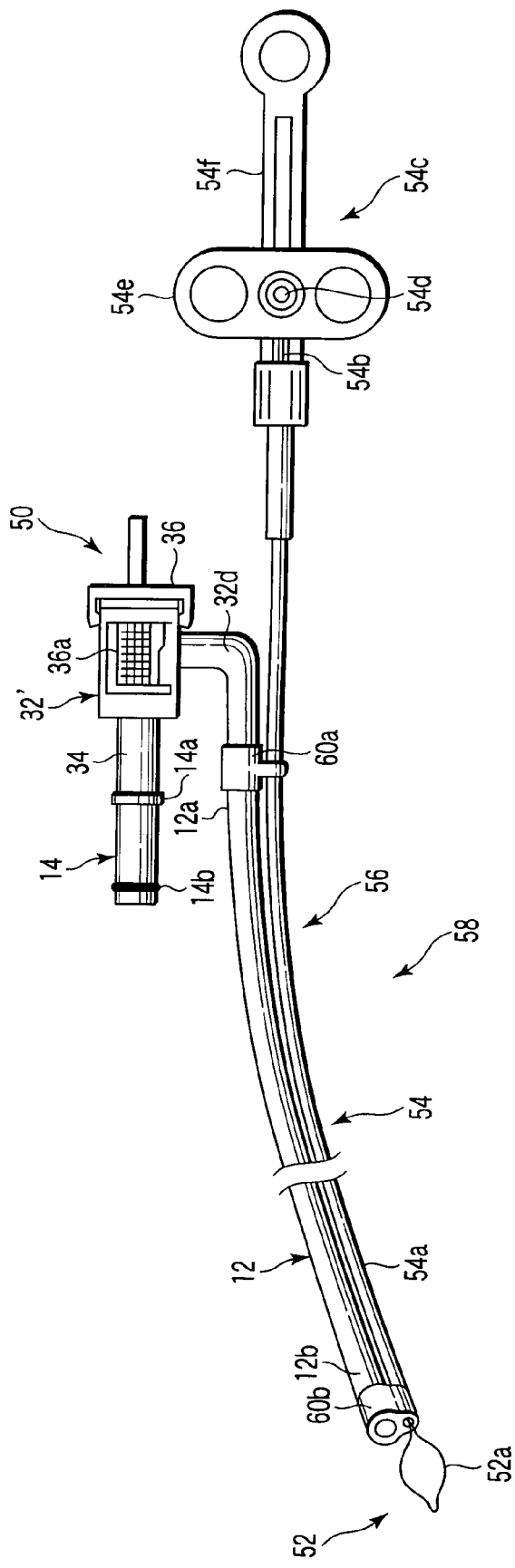
FIG. 9 is a schematic perspective view of an assembly of a suction catheter and a high frequency snare catheter, the assembly being in accordance with a third embodiment of the endoscope accessory of this invention, wherein the suction catheter includes a substance trapping unit, and the high frequency snare catheter includes a high frequency snare, which is a type of a substance handling unit, and a high frequency snare operation unit.
Figure 10:
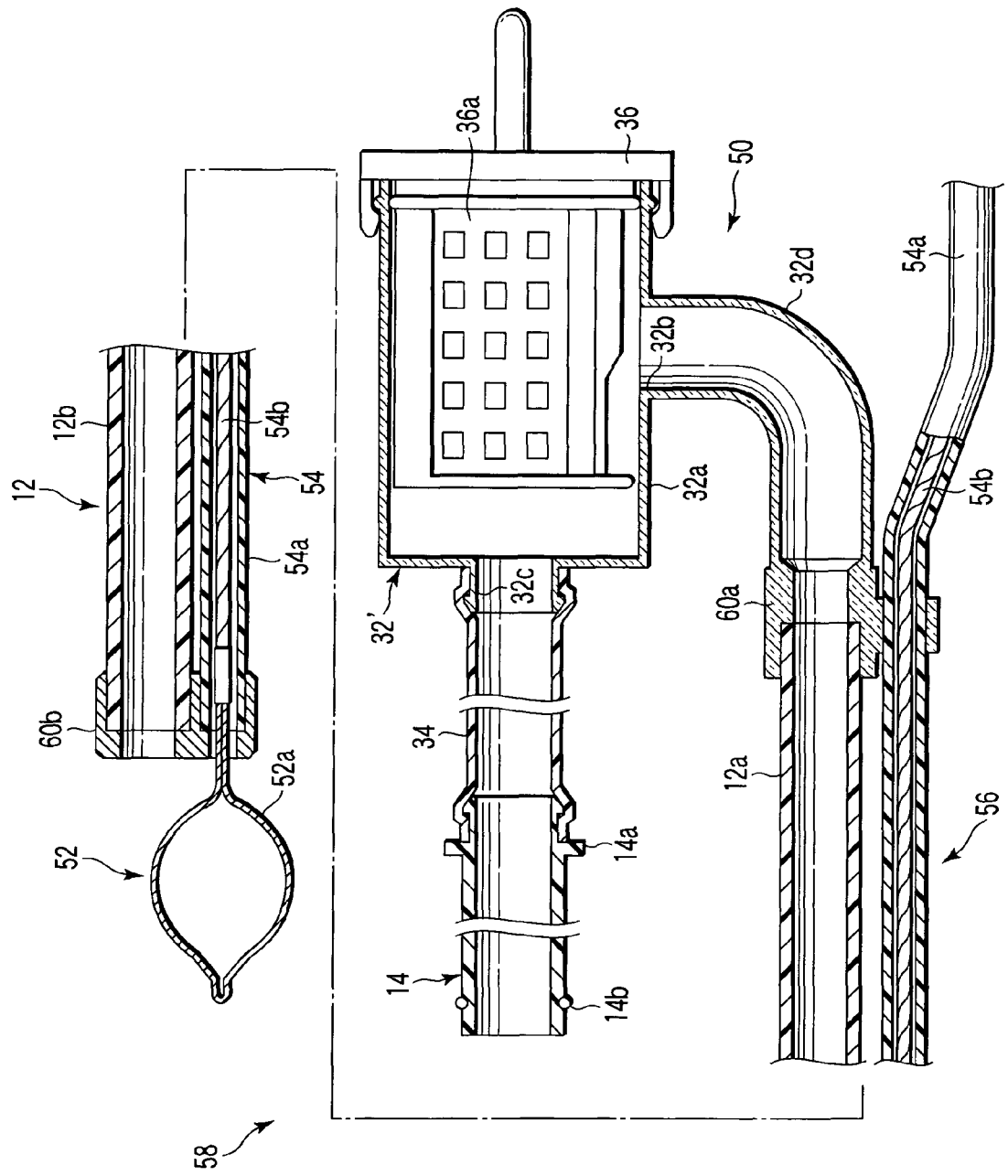
FIG. 10 is an enlarged schematic longitudinal sectional of the suction catheter and the high frequency snare catheter, both catheters included in the assembly of FIG. 9.

FIG. 9 schematically shows a perspective view of the above described assembly 58 according to the third embodiment of the endoscope accessory of this invention, and FIG. 10 schematically shows a longitudinal sectional view of the assembly 58 of FIG. 9 in an enlarged scale.

Most part of components of the suction catheter 50 of the assembly 58 of the third embodiment is the same as that of the suction catheter 30 shown in FIGS. 6 and 7. Thus, the components of the suction catheter 50 which are the same as the components of the suction catheter 30 in FIGS. 6 and 7 are designated by the same reference numerals used to designate the components of the suction catheter 30 in FIGS. 6 and 7 corresponding to those of the suction catheter 50, and the detailed descriptions thereof will be omitted.

Like the suction catheter 30 in FIGS. 6 and 7, the suction catheter 50 further includes a substance trapping unit 32' between the insertion unit 12 and the connection unit 14. The substance trapping unit 32' traps a substance sucked into the inner hole of the insertion unit 12 from the distal end (insertion end) region 12b of the insertion unit 12.

The substance trapping unit 32' includes an insertion unit connection member 32d which is integrally formed with the container 32a with the same material as that of the container 32a and which extends from the entrance opening 32b of the container 32a. The insertion unit connection member 32d extends to be substantially parallel with the connection member 34 in a direction in which the connection member 34 extends. And, the proximal end region 12a of the insertion unit 12 is connected to the extending end region of the insertion unit connection member 32d.

The high frequency snare catheter 56 includes a high frequency snare 52a which is a type of a substance handling unit 52, and a high frequency snare operation unit 54. The high frequency snare operation unit 54 of the high frequency snare catheter 56 has a flexible sheath tube 54a which extends along the insertion unit 12 of the suction catheter 50. The sheath tube 54a is held to the insertion unit 12 to be movable integrally with the insertion unit 12. More specifically, the sheath tube 54a is held at a plurality of positions on the insertion unit 12, which are spaced apart from each other in a longitudinal direction of the insertion unit 12, by a plurality of holding members. In this embodiment, the sheath tube 54a is held at the proximal and distal end regions 12a and 12b of the insertion unit 12 by holding members 60a and 60b.

The holding member 60b at the distal end region 12b of the insertion unit 12 fixes an extending end region of the sheath tube 54a not to allow a movement of the extending end region of the sheath tube 54a along its center line. The holding member 60a at the proximal end region 12a of the insertion unit 12 is integrally formed with the extending end region of the insertion unit connection member 32d of the substance trapping unit 32', and holds the sheath tube 54a so as to make the sheath tube 54a being movable in a direction along the center line thereof so that the insertion unit 12 together with the sheath tube 54a can be freely bendable.

The high frequency snare operation unit 54 has an operation wire 54b which extends in the sheath tube 54a and which has an electrical conductivity and flexibility. A high frequency snare 52a is held by the operation wire 54b in the vicinity of the distal end region 12b of the insertion unit 12, and the high frequency snare 52a is electrically connected to the operation wire 54b. The high frequency snare operation unit 54 further has a high frequency snare operation device 54c which is connected to the operation wire 54b in the vicinity of the proximal end region 12a of the insertion unit 12. The high frequency snare operation device 54c has a slider 54e which is connected to the operation wire 54b and a slider holder 54f which holds the slider 54e to be movable in a predetermined range in a longitudinal direction of the operation wire 54b. The slider 54e includes an electrode 54d which is electrically connected to the operation wire 54b.

When the slider 54e of the high frequency snare operation device 54c is moved in the predetermined range in the longitudinal direction of operation wire 54b, the high frequency snare 52a at the extending end of the operation wire 54b is projected out from and retracted into the extending end region of the sheath tube 54a. The high frequency snare 52a has elasticity. Therefore, the high frequency snare 52a spreads out in a circular shape while it projects out from the extending end region of the sheath tube 54a due to its elastic force as shown in FIGS. 9 and 10. In addition, when the high frequency snare 52a is retracted into the extending end region of the sheath tube 54a, the high frequency snare 52a is pressed by the extending end region of the sheath tube 54a and is closed against the elastic force.

That is, the endoscope accessory according to the third embodiment of this invention, which is shown in FIGS. 9 and 10 and which is constituted by the assembly 58 of the suction catheter 50 and the high frequency snare catheter 56, comprises the high frequency snare 52a which is a type of the substance handling unit 52 near to the distal end region 12b of the insertion unit 12 of the suction catheter 50. Further, the assembly 58 comprises the high frequency snare operation unit 54 which extends along the insertion unit 12 and which is inserted together with the insertion unit 12 into the accessory insertion channel 18c of the insertion portion 18 of the endoscope 16 from the entrance 18d of the accessory insertion channel 18c and which is connected to the high frequency snare 52a as the substance handling unit 52 to operate the high frequency snare 52a.

Next, a method for mounting the suction catheter 50 and the high frequency snare catheter 56 to the endoscope 16 will be described with reference to FIGS. 11A to 12B. By this mounting, the assembly 58 of the suction catheter 50 and the high frequency snare catheter 56, each of which is a type of the endoscope accessory and is configured as described above, is combined with the endoscope 16, which is configured as described above, to constitute the endoscope system according to the third embodiment of this invention. Further, an operation for collecting a substance (for example, a polyp) of a desired region inside a living organism (such as a human) will be described as an example of the method for using the endoscope system according to the third embodiment configured as described above.

The one end region 18a of the insertion portion 18 of the endoscope 16, in the accessory insertion channel 18c of which nothing has been inserted as shown in FIG. 2, is inserted into the living organism (such as a human) until the one end region 18a of the insertion portion 18 reaches a position near to the desired region 38 inside the living organism (such as human). During this time, an operator of the endoscope 16 can view an image in a direction, in which the end surface of the one end region 18a is directed, by the end portion of the abovementioned optical system in the end surface of the one end region 18a.

Figures 11A, 11B, 11C:
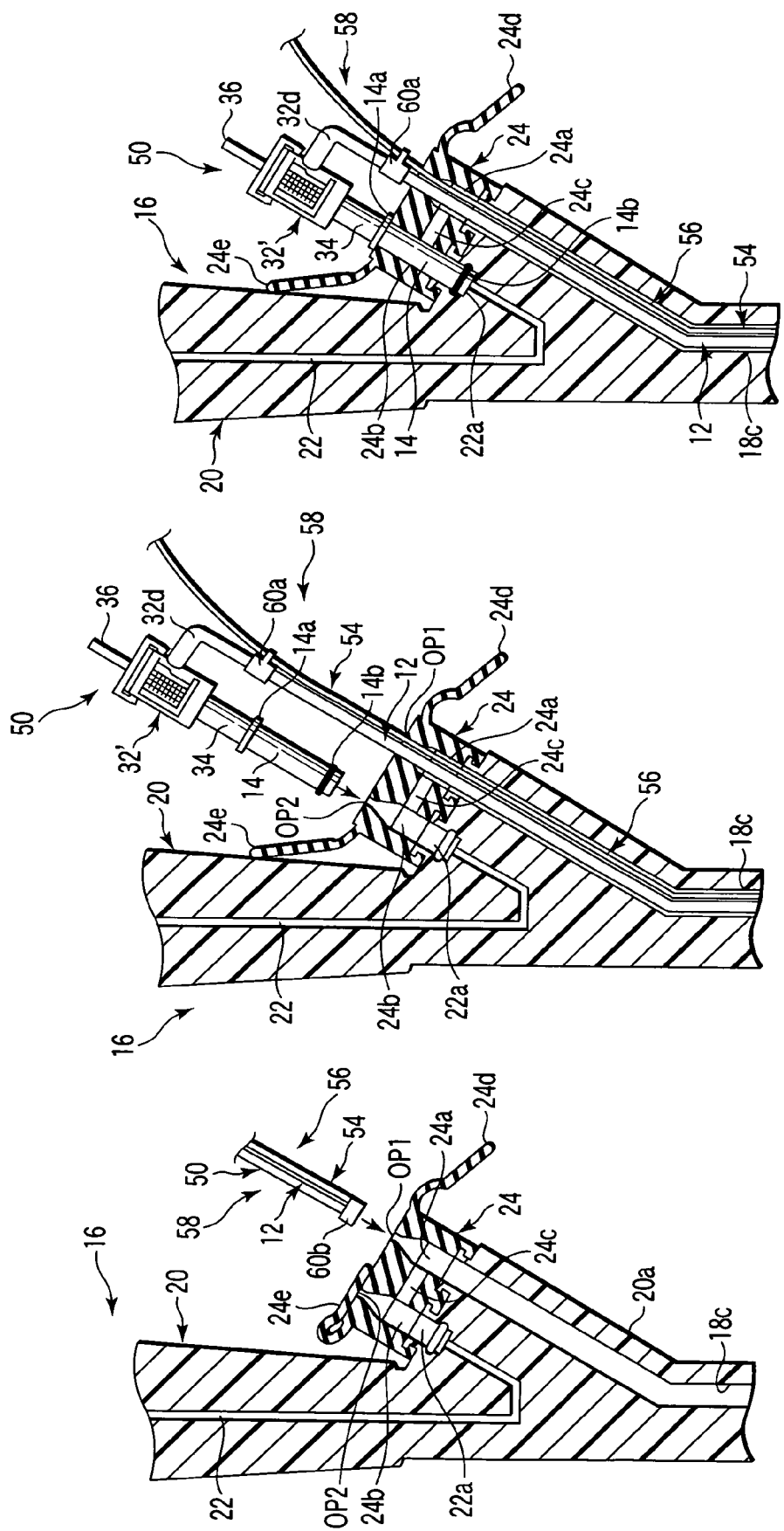
FIG. 11A is an enlarged schematic longitudinal sectional view of the entrance of the accessory insertion channel and the entrance of the suction conduit in the operation portion of the endoscope of FIG. 2, wherein a distal end region of the insertion unit of the suction catheter and a distal end region of the high frequency snare catheter, both catheters included in the assembly of FIG. 9, are in a state immediately before these are inserted into the entrance of the accessory insertion channel to form a third embodiment of the endoscope system of this invention by combining the assembly of FIG. 9 with the endoscope of FIG. 2.
FIG. 11B is a schematic longitudinal sectional view like FIG. 11A, wherein the insertion unit of the suction catheter and the operation unit of the high frequency snare catheter, both catheters included in the assembly of FIG. 9, are inserted into the accessory insertion channel of the endoscope of FIG. 2, and the connection unit of the suction catheter is immediately before it is connected to the entrance of the suction conduit of the endoscope.
FIG. 11C is a schematic longitudinal sectional view like FIG. 11A, wherein the insertion unit of the suction catheter and the operation unit of the high frequency snare catheter, both catheters included in the assembly of FIG. 9, are inserted into the accessory insertion channel of the endoscope of FIG. 2, and the connection unit of the suction catheter is connected to the entrance of the suction conduit of the endoscope.

Next, as shown in FIG. 11A, the first cover 24d of the cap member 24 is opened to expose the narrowed point OP1 of the insertion opening for the insertion unit 24a, and the assembly 58 of the suction catheter 50 and the high frequency snare catheter 56, each of which is a type of endoscope accessory, is inserted into the narrowed point OP1. More specifically, the distal end region 12b of the insertion unit 12 of the suction catheter 50 and the distal end region of the sheath tube 54a of the high frequency snare operation unit 54 are inserted into the narrowed point OP1. In addition, the insertion unit 12 and the sheath tube 54a are moved in the direction along the center line of the accessory insertion channel 18c in the accessory insertion channel 18c until each of the distal end surface of the distal end region 12b of the insertion unit 12 of the suction catheter 50 and the distal end surface of the distal end region of the sheath tube 54a reaches in the vicinity of the opening of the accessory insertion channel 18c in the end surface of the one end region 18a of the insertion portion 18 of the endoscope 16. During this time, the insertion unit 12 and the sheath tube 54a, together with the high frequency snare catheter 40, seal the narrowed point OP1.

Next, as shown in FIG. 11B, the second cover 24e of the cap member 24 is opened to expose the narrowed point OP2 of the insertion opening for the connection unit 24b. Then, the outer end of the connection unit 14 of the suction catheter 50 is inserted into the narrowed point OP2 until the sealing unit 14 on the outer end region (that is, the insertion end region) of the connection unit 14 detachably engages with the circular groove in the entrance 22a of the suction conduit 22, as shown in FIG. 1C. During this time, the connection unit 14 seals the narrowed point OP2, and closes the communication between the insertion opening for the insertion unit 24a and the insertion opening for the connection unit 24b by the communication hole 24c in the cap member 24 so that the communication between the accessory insertion channel 18c and the suction conduit 22 is closed.

At this time, as shown in FIG. 12A, each of the end surface of the distal end region 12b of the insertion unit 12 and the end surface of the distal end region of the sheath tube 54a projects from the opening of the accessory insertion channel 18c in the end surface of the one end region 18a of the insertion portion 18 of the endoscope 16 and moves to the desired region 62 inside the living organism (such as human).

Next, the high frequency snare operation device 54c of the high frequency snare catheter 56, which is exposed in the outside of the cap member 24 of the projection 20a of the operation portion 20 of the endoscope 16, is operated to project the high frequency snare 52a at the distal end of the high frequency snare catheter 56 toward the desired region 62 inside the living organism (such as human) from the extending end of the sheath tube 54a and to cut out a portion (polyp) 62a of the desired region 62.

Next, the operator operates the high frequency snare operation device 54c to retract the high frequency snare 52a of the high frequency snare catheter 56 into the distal end of the sheath tube 54a, and then the operator operates the suction device 26 (see FIG. 2) of the endoscope 16. As a result of this, the portion (polyp) 62a is sucked into the inner hole of the insertion unit 12 from the distal end region 12b of the insertion unit 12. The portion (polyp) 62a which is sucked into the inner hole of the insertion unit 12 is entered into the container 32a of the substance trapping unit 32' through the entrance opening 32b and is trapped on the trap member 36a.

The portion (polyp) 62a trapped on the trap member 36a can be collected from the trap member 36a after the operation of the suction device 26 of the endoscope 16 is stopped and then the cover 36 together with the trap member 36a is removed from the container 32a.

If there is a substance (such as body fluid, other fluid or food residues) which is sucked together with the portion (polyp) 62a into the inner hole of the insertion unit 12 from the desired region 62 inside the living organism (such as a human), the substance which passes through the trap member 36a in the container 32a of the substance trapping unit 32' is further sucked into the suction conduit 22 of the endoscope 16 via the connection unit 14 connected to the exit opening 32c by the connection member 34, and then is collected in the aforementioned liquid container (not shown) of the suction device 26.

In the assembly 58 of the suction catheter 50 and the high frequency snare catheter 56, according to the third embodiment of the endoscope accessory of this invention, and the endoscope system including the assembly 58 and according to the third embodiment of the endoscope system of this invention, can obtain the same advantages as those obtained by the suction catheter 30 of FIG. 6 and by the endoscope system which includes the suction catheter 30. In addition, since the suction catheter 50 and the high frequency snare catheter 56 constitute the assembly 58, the suction catheter 50 and the high frequency snare catheter 56 can be inserted into and drawn out from the accessory insertion channel 18c of the endoscope 16 as one unit. Therefore, the operation to collect the portion 62a of the desired region 62 from the desired region 62 inside the living organism (such as human) can be performed even more easily.

In this embodiment, the high frequency snare 52a as the substance handling unit 25 is arranged near to the distal end region (insertion end region) 12b of the insertion unit 12 of the suction unit 50. However, according to the aspect of this invention, various well known substance handling unit catheters excluding the high frequency snare 52a may be combined with the suction catheter 50 to arrange the various well known substance handling unit catheters near to the distal end region (insertion end region) 12b of the insertion unit 12 of the suction unit 50 as far as the various well known substance handling unit catheters together with the insertion unit 12 of the suction catheter 50 can be inserted into the accessory insertion channel 18c of the endoscope 16 and can be moved in the accessory insertion channel 18c in the direction along the center line of the accessory insertion channel 18c.

Fourth Embodiment

Next, an assembly 66 of the suction catheter 50 and the high frequency snare catheter 56 which includes the high frequency snare 52a as a type of the substance handling unit 52 and the high frequency snare operation unit 54, according to a fourth embodiment of the endoscope accessory of this invention will be described with reference to FIGS. 13A and 13B in the attached drawings.

Most part of components of the assembly 66 of the fourth embodiment is the same as that of the assembly 58 shown in FIGS. 9 and 10. Thus, the components of the assembly 66 of the fourth embodiment which are the same as the components of the assembly 58 of the third embodiment in FIGS. 9 and 10 are designated by the same reference numerals used to designate the components of the assembly 58 in FIGS. 9 and 10 corresponding to those of the assembly 66 of the fourth embodiment, and the detailed descriptions thereof will be omitted.

The assembly 66 of the fourth embodiment is different from the assembly 58 of the third embodiment in that the high frequency snare catheter 56 is detachably held on the suction catheter 50.

For this configuration, in this embodiment, holding members 60'a and 60'b at the proximal end region 12a and distal end region 12b of the insertion unit 12 of the suction catheter 50 include elastic clips EC1 and EC2 which elastically hold a distal end region LR and a middle region MR of the sheath tube 54a of the high frequency snare operation unit 54 of the high frequency snare catheter 56.

And, the elastic clip EC1 of the holding member 60'a at the proximal end region 12a of the insertion unit 12 holds the middle region MR of the sheath tube 54a so as to make the sheath tube 54a being movable in a direction along the center line thereof so that the insertion unit 12 together with the sheath tube 54a can be freely bendable. And, the elastic clips EC2 of the holding member 60'b at the distal end region 12b of the insertion unit 12 hold the distal end region LR of the sheath tube 54a not to allow a movement of the distal end region of the sheath tube 54a along its center line.

The elastic clips EC1 and EC2 of the holding members 60'a and 60'b can be integrally formed with the holding members 60'a and 60'b with the same material as that of the holding members 60'a and 60'b. Alternatively, the elastic clips EC1 and EC2 may be formed independent of the holding members 60'a and 60'b and then the elastic clips EC1 and EC2 may be attached to the holding members 60'a and 60'b, FIG. 13A shows that the suction catheter 50 with the substance trapping unit 32', and the high frequency snare catheter 56, both of which are included in the assembly 66 of the fourth embodiment of the endoscope assembly of this invention, are separated from each other.

Figure 13A:
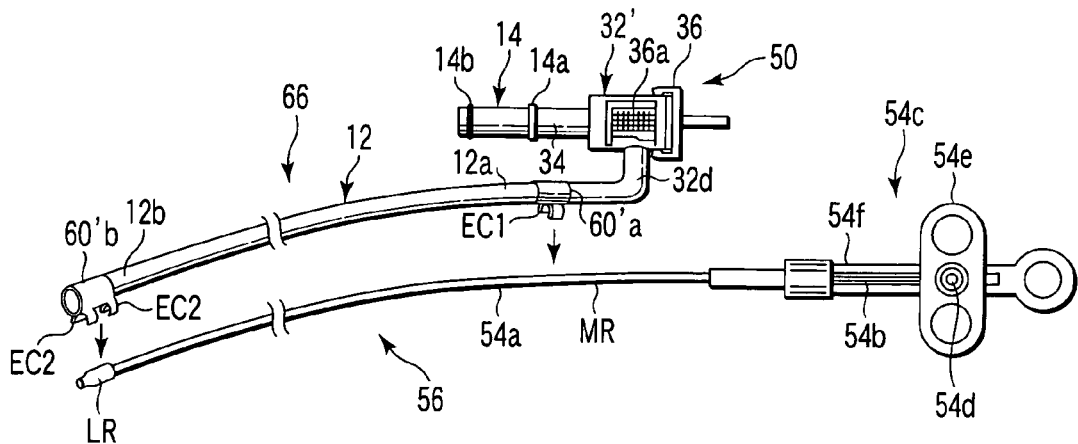
FIG. 13A is a schematic perspective view of an assembly of a suction catheter and a high frequency snare catheter, the assembly being in accordance with a fourth embodiment of the endoscope accessory of this invention, wherein the suction catheter includes a substance trapping unit, and the high frequency snare catheter includes a high frequency snare, which is a type of a substance handling unit, and a high frequency snare operation unit, and wherein the suction catheter and the high frequency snare catheter are separated from each other.
Figure 13B:
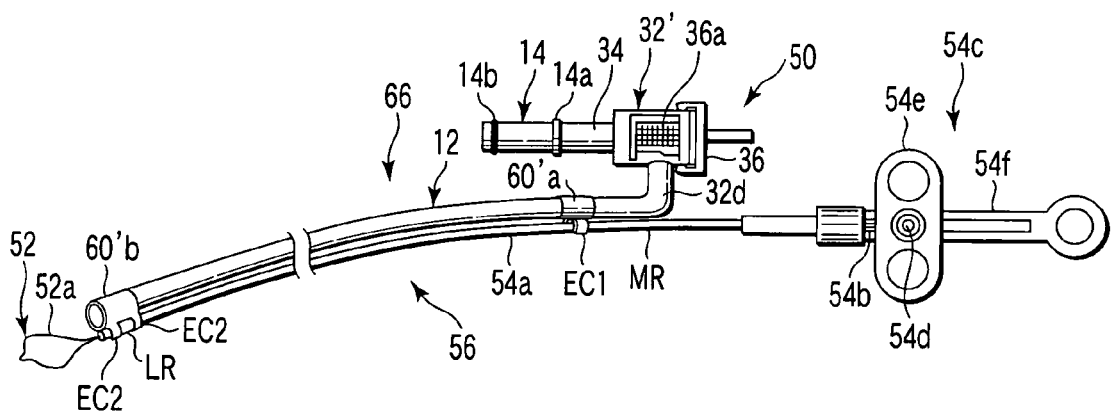
FIG. 13B is a schematic perspective view, wherein the suction catheter including the substance trapping unit and the high frequency snare catheter, both catheters separated from each other in FIG. 13A, are joined together to form the assembly.

FIG. 13B shows that the suction catheter 50 with the substance trapping unit 32', and the high frequency snare catheter 56, both of which are separated from each other in FIG. 13A, are assembled with each other to constitute the assembly 66 by the holding members 60'a and 60'b at the proximal end region 12a and distal end region 12b of the insertion unit 12 of the suction catheter 50.

The assembly 66 shown in FIG. 13B, like the assembly 58 shown in FIGS. 9 and 10, can be mounted on and combined with the endoscope 16 shown in FIG. 2 to form a fourth embodiment of the endoscope system of this invention.

And, the assembly 66 shown in FIG. 13B and the endoscope system including the assembly 66 obtain the same technical advantages as those obtained by the assembly 58 shown in FIGS. 9 and 10 and the endoscope system including the assembly 58.

Further, even if one of the suction catheter 50 and the high frequency snare catheter 56 is broken, only the broken one can be replaced with new one.

Naturally, according to the aspect of this invention, various well known substance handling unit catheters excluding the high frequency snare 52a may be combined with the suction catheter 50 to arrange the various well known substance handling unit catheters near to the distal end region (insertion end region) 12b of the insertion unit 12 of the suction unit 50 as far as the various well known substance handling unit catheters together with the insertion unit 12 of the suction catheter 50 can be inserted into the accessory insertion channel 18c of the endoscope 16 and can be moved in the accessory insertion channel 18c in the direction along the center line of the accessory insertion channel 18c.

Fifth Embodiment

Next, an assembly 78 of a suction catheter 70 and a biopsy forceps catheter 76, according to a fifth embodiment of the endoscope accessory of this invention, a method for mounting the assembly 78 onto the endoscope 16 to constitute a fifth embodiment of the endoscope system of this invention, and an example of a method for using the endoscope system will be described with reference to FIGS. 14 to 17D in the attached drawings.

Some components of the suction catheter 70 of the assembly 78 of the fifth embodiment are the same as those of the suction catheter 50 of the third embodiment shown in FIGS. 9 and 10. Thus, the components of the suction catheter 70 which are the same as the components of the suction catheter 30 in FIGS. 6 and 7 are designated by the same reference numerals used to designate the components of the suction catheter 30 in FIGS. 6 and 7 corresponding to those of the suction catheter 50, and the detailed descriptions thereof will be omitted.

Figure 14:
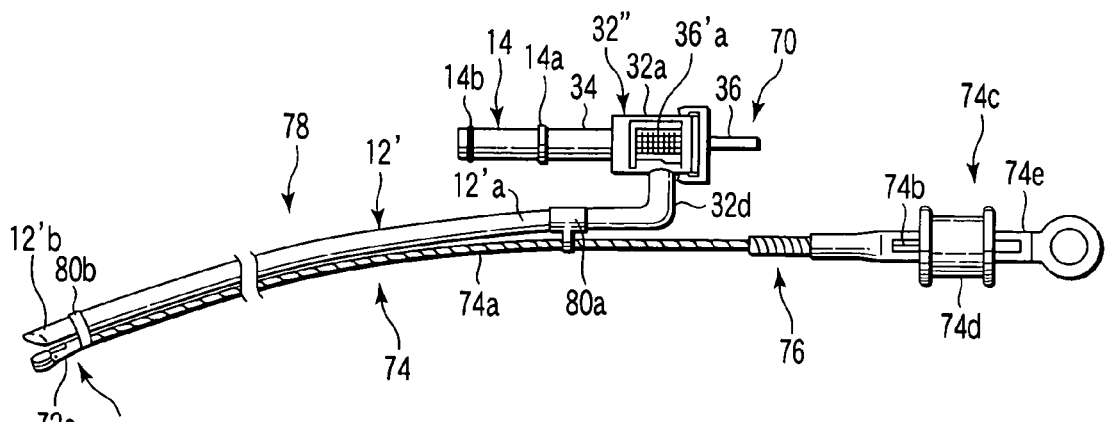
FIG. 14 is a schematic perspective view of an assembly of a suction catheter and a biopsy forceps catheter, the assembly being in accordance with a fifth embodiment of the endoscope accessory of this invention, wherein the suction catheter includes a substance trapping unit, and the biopsy forceps catheter includes biopsy forceps, which is a type of substance handling unit, and a biopsy forceps operation unit.

FIG. 14 schematically shows a perspective view of the above described assembly 78 of the suction catheter 70 and the biopsy forceps catheter 76, according to the fifth embodiment of the endoscope accessory of this invention. As apparent from FIG. 14, the biopsy forceps catheter 76 includes biopsy forceps 72a, which is a type of a substance handling unit 72, and a biopsy forceps operation unit 74.

Like the suction catheter 30 in FIGS. 6 and 7, the suction catheter 70 further includes a substance trapping unit 32" between the insertion unit 12' and the connection unit 14. The substance trapping unit 32" traps a substance sucked into the inner hole of the insertion unit 12' from the distal end (insertion end) region 12'b of the insertion unit 12'.

Figure 15:
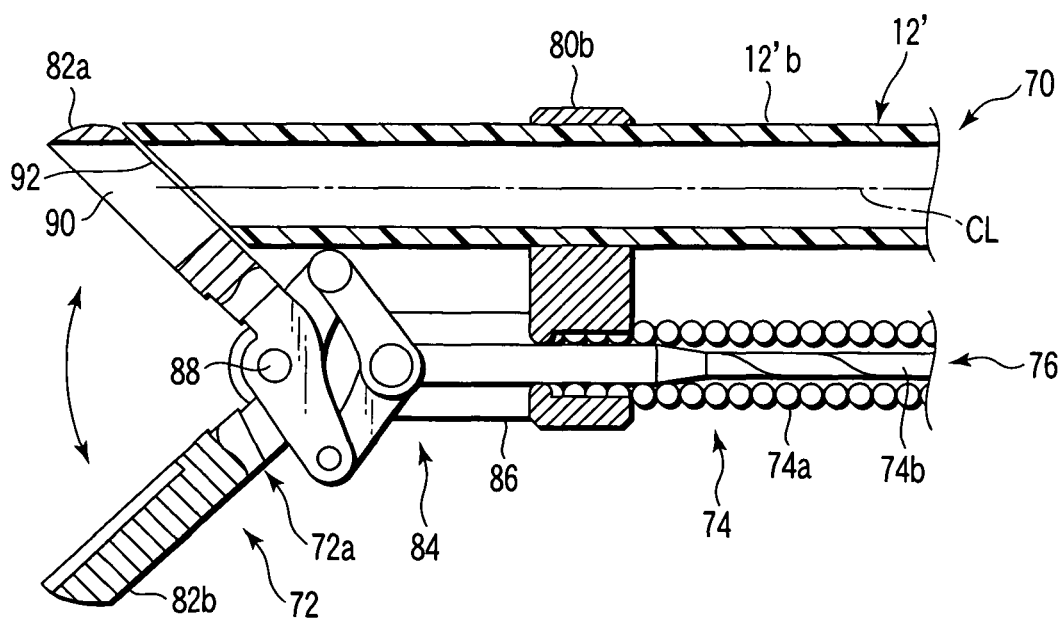
FIG. 15 is an enlarged schematic longitudinal sectional view of a distal end region of the insertion unit of the suction catheter with the substance trapping unit and a distal end region of the biopsy forceps catheter in the assembly of FIG. 14.
Figure 16:
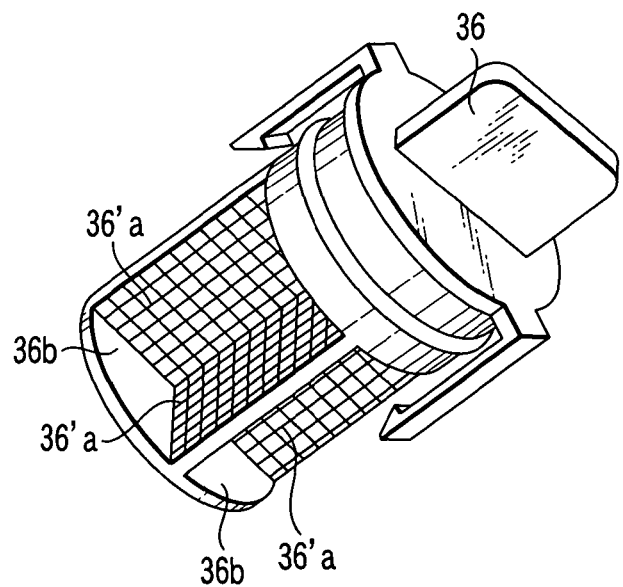
FIG. 16 is a schematic perspective view of a trap of the substance trapping unit of the suction catheter including the substance trapping unit in the assembly of FIG. 14.

FIG. 15 schematically shows a longitudinal sectional view of the distal end (insertion end) region 12'b of the insertion unit 12' of the suction catheter 70 of FIG. 14 and the biopsy forceps 72a, which is a type of the substance handling unit 72 and which is arranged near to the distal end (insertion end) region 12'b.

The structure of the insertion unit 12' of the suction catheter 70 of FIG. 14 is slightly different from that of the insertion unit 12 of the suction catheter 30 of FIGS. 6 and 7. Specifically, the distal end surface of the distal end (insertion end) region 12b of the insertion unit 12 of the suction catheter 30 of FIGS. 6 and 7 crosses the center line of the insertion unit 12 at right angles, but the distal end face of the distal end (insertion end) region 12'b of the insertion unit 12' of the suction catheter 70 of FIG. 14 inclines with respect to a center line CL of the insertion unit 12'.

The structure of the substance trapping unit 32" of FIG. 14 is slightly different from that of the substance trapping unit 32' of the suction catheter 30 of FIGS. 6 and 7. Specifically, the cover 36 detachably attached to the open end of the container 32a includes four mesh-like trapping members 36'a which partition the inner space of the container 32a into four sections. And, by rotating the cover 36 for a predetermined angles relative to the one end opening of the container 32a of the substance trapping unit 32", any one of the four sections 36b between the four mesh-like trapping members 36'a can be faced the entrance opening 32b of the container 32a.

The biopsy forceps operation unit 74 of the biopsy forceps catheter 76 has a flexible coil sheath tube 74a which extends along the insertion unit 12' of the suction catheter 70. The coil sheath tube 74a is held to the insertion unit 12' to be movable integrally with the insertion unit 12'. Particularly, the coil sheath tube 74a is held at a plurality of positions on the insertion unit 12', which are spaced apart from each other in a longitudinal direction of the insertion unit 12', by a plurality of holding members. In this embodiment, the coil sheath tube 74a is held at the proximal and distal end regions 12'a and 12'b of the insertion unit 12' by holding members 80a and 80b.

The holding member 80b at the distal end region 12'b of the insertion unit 12' fixes an extending end region of the coil sheath tube 74a not to allow a movement of the extending end region of the coil sheath tube 74a along its center line. The holding member 80a at the proximal end region 12'a of the insertion unit 12' is integrally formed with the extending end region of the insertion unit connection member 32d of the substance trapping unit 32", and holds the coil sheath tube 74a so as to make the coil sheath tube 74a being movable in a direction along the center line thereof so that the insertion unit 12' together with the coil sheath tube 74a can be freely bendable.

The biopsy forceps operation unit 74 has a flexible operation wire 74b which extends in the coil sheath tube 74a. The biopsy forceps 72a which is a type of the substance handling unit 72 is held by the operation wire 74b in the vicinity of the distal end region 12'b of the insertion unit 12'.

The biopsy forceps operation unit 74 further has a biopsy forceps operation device 74c which is connected to the operation wire 74b in the vicinity of the proximal end region 12'a of the insertion unit 12'. The biopsy forceps operation device 74c has a slider 74d which is connected to the operation wire 74b and a slider holder 74e which holds the slider 74d to be movable in a predetermined range in a longitudinal direction of the operation wire 74b.

As shown in FIG. 15, the biopsy forceps 72a includes a pair of forceps cups 82a, 82b which can open and close and a forceps cups open and close mechanism 84 which makes the pair of forceps cups 82a, 82b open and close by the movement of the operation wire 74b within the above described predetermined range in the longitudinal direction of the operation wire 74b. More specifically, the biopsy forceps 72a includes a supporting member 86 which is supported at the holding member 80b on the distal end region 12'b of the insertion unit 12', a rotational center shaft 88, which is supported by the supporting member 86 and which connects the pair of forceps cups 82a, 82b to the supporting member 86 to being able to be opened and closed, and a pantograph mechanism which is interposed between the pair of forceps cups 82a, 82b and the operation wire 74b and which functions as the forceps cups open and close mechanism 84.

When the pair of forceps cups 82a, 82b are opened, an outer surface of one forceps cup 82a comes into contact with the slanted distal end surface of the distal end (insertion end) region 12'b of the insertion unit 12' of the suction catheter 70, as shown in FIG. 15. A substance holding hollow 90 is formed in an inner surface of the one forceps cup 82a, and a through hole 92 is formed in the outer surface of the one forceps cup 82a to communicate with the substance holding hollow 90.

That is, the endoscope accessory which is constituted by the assembly 78 of the suction catheter 70 and the biopsy forceps catheter 76, shown in FIGS. 14 and 15, and which is according to the fifth embodiment of this invention, comprises the biopsy forceps 72a as a type of the substance handling unit 72 in the vicinity of the distal end (insertion end) region 12'b of the insertion unit 12' of the suction catheter 70. Further, the assembly 78 comprises the biopsy forceps operation unit 74 which extends along the insertion unit 12' and which is inserted together with the insertion unit 12' into the accessory insertion channel 18c of the insertion portion 18 of the endoscope 16 from the entrance 18d of the accessory insertion channel 18c and which is connected to the biopsy forceps 72a as the substance handling unit 72 to operate the biopsy forceps 72a.

Next, with reference to FIGS. 17A to 17D, an operation for collecting a substance (for example, a mucous membrane) of a desired region inside a living organism (such as a human) will be described as an example of the method for using the endoscope system according to the fifth embodiment configured as described above.

Figure 17A:
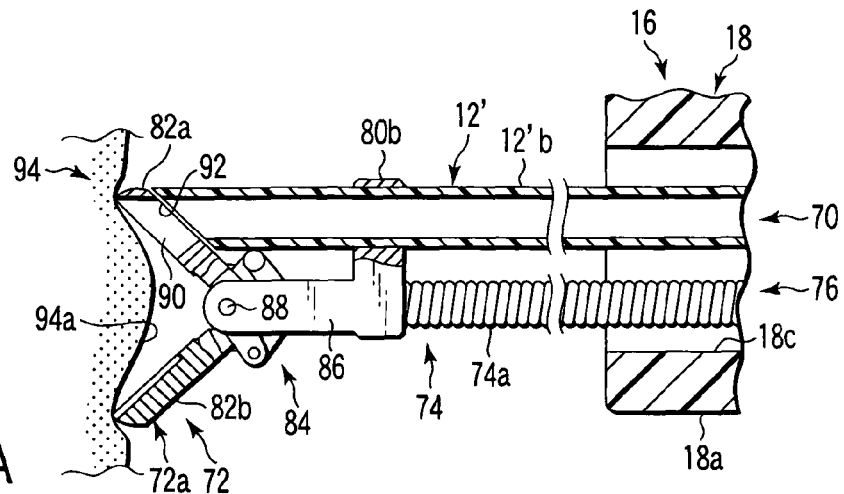
FIGS. 17A, 17B, 17C and 17D are schematic longitudinal sectional views sequentially showing that a portion of a desired region inside a human body is grasped and collected by the biopsy forceps and the suction catheter, after the assembly of FIG. 14 is combined with the endoscope of FIG. 2 to form a fifth embodiment of the endoscope system of this invention, and one end region of the insertion portion of the endoscope of FIG. 2 of the endoscope system is disposed in the vicinity of a desired region inside a human body, and then a distal end region of the insertion unit of the suction catheter and a distal end region of the biopsy forceps catheter in the assembly of FIG. 14 are caused to protrude from the opening of the accessory insertion channel in the one end region of the insertion portion of the endoscope.

The one end region 18a of the insertion portion 18 of the endoscope 16, in the accessory insertion channel 18c of which nothing has been inserted as shown in FIG. 2, is inserted into the living organism (such as a human) until the one end region 18a of the insertion portion 18 reaches a position near to the desired region 94 inside the living organism (such as human) as shown in FIG. 17A. During this time, an operator of the endoscope 16 can view an image in a direction, in which the end surface of the one end region 18a is directed, by the end portion of the abovementioned optical system in the end surface of the one end region 18a.

The assembly 78 shown in FIG. 14 like the assembly 58 shown in FIGS. 9 and 10 can be mounted on and combined with the endoscope 16 shown in FIG. 2 and can constitute the fifth embodiment of the endoscope system of this invention.

At this time, as shown in FIG. 17A, each of the end surface of the distal end region 12'b of the insertion unit 12' and the end surface of the distal end region of the coil sheath tube 54a projects from the opening of the accessory insertion channel 18c in the end surface of the one end region 18a of the insertion portion 18 of the endoscope 16 and moves to the desired region 94 inside the living organism (such as human).

Next, the operator operates the biopsy forceps operation device 74c (see FIG. 14) of the biopsy forceps catheter 76, which is exposed in the outside of the cap member 24 of the projection 20a of the operation portion 20 of the endoscope 16, to open the pair of the forceps cups 82a, 82b of the biopsy forceps 72a at the distal end of the biopsy forceps catheter 76 and to locate the forceps cups 82a, 82b at both sides of a part (a mucous membrane) 94a of the desired region 94 inside the living organism (such as human).

Figure 17B:
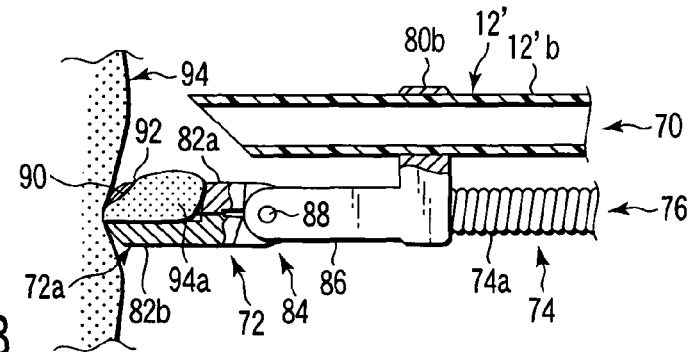
Figure 17C:
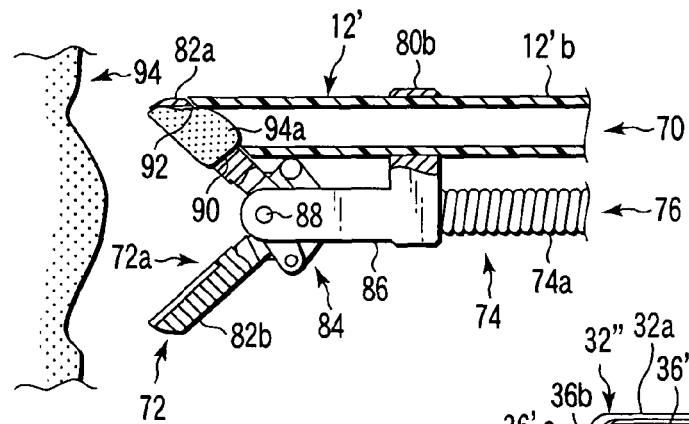
Figure 17D:
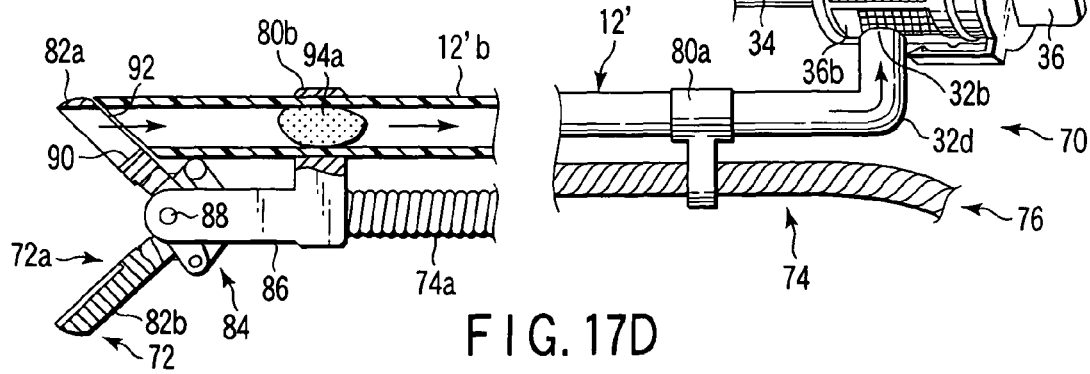

Next, the operator operates the biopsy forceps operation device 74c (see FIG. 14) of the biopsy forceps catheter 76 to close the pair of the forceps cups 82a, 82b of the biopsy forceps 72a at the distal end of the biopsy forceps catheter 76 and to grasp the part (a mucous membrane) 94a of the desired region 94 inside the living organism (such as human) by the pair of the closed forceps cups 82a, 82b, as shown in FIG. 17B.

At this time, the part (a mucous membrane) 94a in the pair of the forceps cups 82a, 82b is held in the substance holding hollow 90 of the one forceps cup 82a.

Next, the operator operates the biopsy forceps operation device 74c (see FIG. 14) of the biopsy forceps catheter 76 to reopen the pair of the forceps cups 82a, 82b of the biopsy forceps 72a at the distal end of the biopsy forceps catheter 76 and to abut the outer surface of the one forceps cup 82a against the slanted distal end surface of the distal end region 12'b of the insertion unit 12' of the suction catheter 70. With this abutment, the through hole 92 in the outer surface of the one forceps cup 82a faces the opening of the inner hole of the insertion unit 12' in the distal end surface of the distal end region 12'b of the insertion unit 12'.

Then, the operator operates the suction device 26 (see FIG. 2) of the endoscope 16. As a result of this, the part (a mucous membrane) 94a in the substance holding hollow 90 of the one forceps cup 82a is sucked into the inner hole of the insertion unit 12' through the through hole 92 in the outer surface of the one forceps cup 82a and the opening of the inner hole of the insertion unit 12' in the distal end surface of the distal end region 12'b of the insertion unit 12'. The part (a mucous membrane) 94a sucked into the inner hole of the insertion unit 12' is entered into the container 32a of the substance trapping unit 32" through the entrance opening 32b and is trapped on the trap member 36'a in the section 36b in the inner space of the container 32a corresponding to the entrance opening 32b.

The inner space of the container 32a of the substance trapping unit 32" of this embodiment is sectioned into the plurality of sections 36b by the plurality of trap members 36'a, and each of the plurality of sections 36b can face the entrance opening 32b of the container 32a by rotating the cover 36 relative to the one open end of the container 32a. Therefore, in a case that the end face of the one end region 18a of the insertion portion 18 of the endoscope 16 is directed to a plurality of desired regions inside the living organism (such as a human) successively and then parts of the plural desired regions are collected successively by using the biopsy forceps catheter 76 and the suction catheter 70 while the one end region 18a of the insertion portion 18 of the endoscope 16 is stayed in the living organism (such as human), the successively collected parts can be trapped successively in the plural sections 36b by rotating the cover 36 of the substance trapping unit 32" intermittently after one collected part is trapped on one trap member 36'a in one section 36b.

The parts (mucous membranes) 94a trapped on the trap members 36'a can be collected from the trap members 36'a after the operation of the suction device 26 of the endoscope 16 is stopped and then the cover 36 together with the trap members 36'a is removed from the container 32a.

If there is a substance (such as body fluid, other fluid or food residues) which is sucked together with the part (a mucous membrane) 94a from the desired region 94 inside the living organism (such as a human) into the inner hole of the insertion unit 12' through the distal end region 12'b of the insertion unit 12', the substance which passes through the trap members 36'a in the container 32a of the substance trapping unit 32" is further sucked into the suction conduit 22 of the endoscope 16 via the connection unit 14 connected to the exit opening 32c of the container 32a by the connection member 34, and then is collected in the aforementioned liquid container (not shown) of the suction device 26.

In the assembly 78 of the suction catheter 70 and the biopsy forceps catheter 76, according to the fifth embodiment of this invention, and the endoscope system including the assembly 78 and according to the fifth embodiment of the endoscope system of this invention, can obtain the same advantages as those obtained by the suction catheter 30 of FIG. 6 and by the endoscope system which includes the suction catheter 30. In addition, since the suction catheter 70 and the biopsy forceps catheter 76 constitute the assembly 78, the suction catheter 70 and the biopsy forceps catheter 76 can be inserted into and drawn out from the accessory insertion channel 18c of the endoscope 16 as one unit. Therefore, the operation to collect the part 94a of the desired region 94 from the desired region 94 inside the living organism (such as human) can be performed even more easily.

[Modification]

Next, a modification of the assemble 78 according to the fifth embodiment of the endoscope accessory of this invention and described above with reference to FIGS. 14 to 17D, will be described with reference to FIGS. 18A and 18B.

Figure 18A:
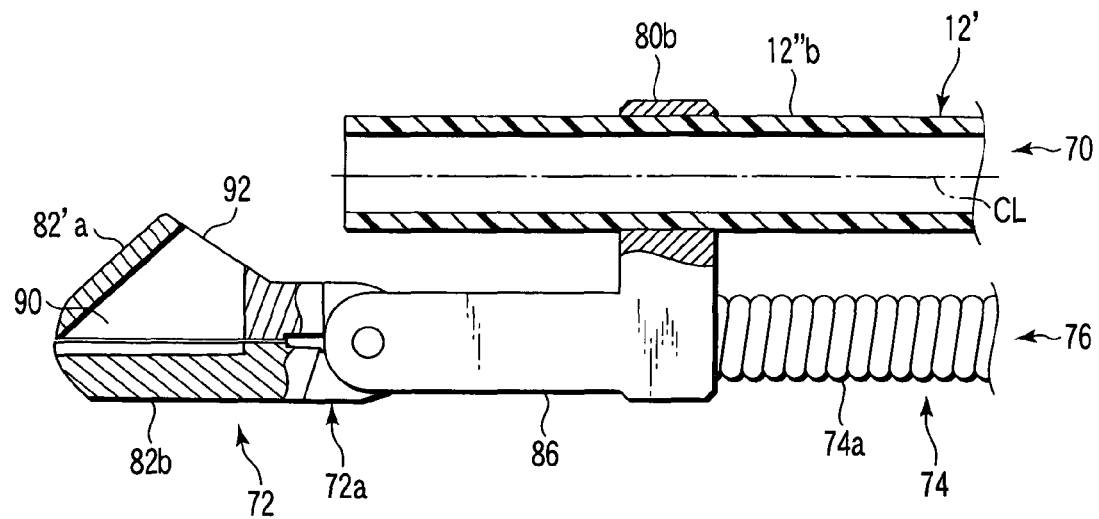
FIG. 18A is an enlarged schematic longitudinal sectional view of an distal end region of a modification of the assembly according to the fifth embodiment of the endoscope accessory of this invention, wherein the biopsy forceps are arranged in a closed position.
Figure 18B:
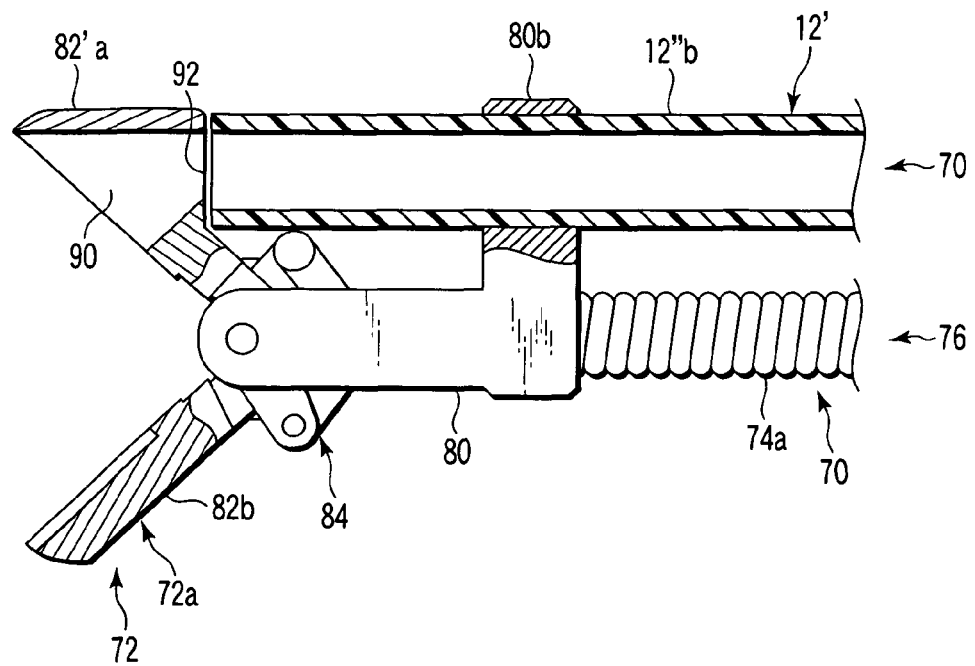
FIG. 18B is an enlarged schematic longitudinal sectional of the distal end region of the assembly of 18A, wherein the biopsy forceps are arranged in an open position to cooperate with the insertion unit of the suction catheter.

Most part of components of the modification shown in FIGS. 18A and 18B is the same as that of the assembly 78 according to the fifth embodiment described above. Thus, the components of the modification shown in FIGS. 18A, 18B which are the same as the components of the assembly 78 in FIGS. 14 to 17D are designated by the same reference numerals used to designate the components of the assembly 78 in FIGS. 14 to 17D corresponding to those of the modification, and the detailed descriptions thereof will be omitted.

This modification is different from the assembly 78 according to the fifth embodiment described above in that the distal end surface of the distal end region 12" of the insertion unit 12' of the suction catheter 70 crosses the center line CL of the inner hole of the insertion unit 12' at right angles as shown in FIG. 18A, and that the height of the outer surface of the one forceps cup 82'a in the pair of forceps cups 82'a, 82b of the biopsy forceps 72a of the biopsy forceps catheter 76 is set larger to neighbor the through hole 92 in the outer surface of the one forceps cup 82'a on the opening of the inner hole of the insertion unit 12' in the distal end surface of the distal end region 12" of the insertion unit 12' when the pair of forceps cups 82'a, 82b is opened.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope accessory used in combination with an endoscope, the endoscope including:

an insertion portion which has a first end region, a second end region, and an accessory insertion channel extending between the first end region and the second end region in the insertion portion and having an entrance in the second end region and an exit opened at the first end region, the first end region being configured to be inserted into a living organism, and an operation portion which is provided at the second end region of the insertion portion, in which a suction conduit is formed, the suction conduct having an entrance and an exit both of which are opened at different points in an outer surface of the operation portion, and the exit of the suction conduit being configured for communicating with a suction device, the entrance of the suction conduit and the entrance of the accessory insertion channel in the outer surface being opened and disposed side by side, and wherein a communication path is formed in a region of the operation portion near the entrances to communicatively connect the suction conduit and the accessory insertion channel with each other, and the endoscope accessory comprising:

a tubular insertion unit which has a distal end region and a proximal end region, the distal end region being configured to be detachably inserted into the accessory insertion channel through the entrance of the accessory insertion channel and to be movable along the accessory insertion channel; and a tubular connection unit which is provided at the proximal end region of the insertion unit and which is configured to be detachably connected to the entrance of the suction conduit, the tubular connection unit including a sealing unit which seals a gap between the tubular connection unit and the entrance of the suction conduit and which seal a communication between the communication path and the suction conduit when the tubular connection unit is detachably connected to the entrance of the suction conduit, so that a suction force from the suction device through the suction conduit is supplied to the tubular insertion unit through the tubular connection unit.

2. The endoscope accessory according to claim 1, further comprising:

a substance trapping unit which is configured to trap a substance sucked through an inner hole of the insertion unit from the distal end region of the insertion unit in an area between the insertion unit and the connection unit.

3. The endoscope accessory according to claim 1, wherein a material of one part of the operation portion of the endoscope, which includes the entrance of the suction conduit, the entrance of the accessory insertion channel, and the communication path, is different from a material of the other part of the operation portion, and the material of the one part is more elastic than the material of the other part.

4. An endoscope system comprising an endoscope and an endoscope accessory, the endoscope including:

an insertion portion which has one end region, an other end region, and an accessory insertion channel extending between the one end region and the other end region in the insertion portion and having an entrance in the other end region and an exit opened at the one end region, at least the one end region being configured to be inserted into a living organism, and an operation portion which is provided at the other end region of the insertion portion, in which a suction conduit is formed, the suction conduit having an entrance and an exit both of which are opened at different points in an outer surface of the operation portion, and the exit of the suction conduit being in communication with a suction device, the entrance of the suction conduit and the entrance of the accessory insertion channel in the outer surface being opened and disposed side by side, and wherein a communication path is formed in a region of the operation portion near to the entrances of the suction conduit and accessory insertion channel, to communicate both of the suction conduit and the accessory insertion channel with each other, and the endoscope accessory including:

a tubular insertion unit which has a distal end region and a proximal end region, the distal end region being configured to be detachably inserted into the accessory insertion channel from the entrance of the accessory insertion channel and to be movable along the accessory insertion channel, and a tubular connection unit which is provided at the proximal end region of the tubular insertion unit and which is configured to be detachably connected to the entrance of the suction conduit and to close the communication between the communication path and the suction conduit, the tubular connection unit including a sealing unit which seals a gap between the tubular connection unit and the entrance of the suction conduit and which seals a communication between the communication path and the suction conduit when the tubular connection unit is detachably connected to the entrance of the suction conduit, so that a suction force from the suction device through the suction conduit is supplied to the tubular insertion unit through the tubular connection unit.

5. The endoscope system according to claim 4, wherein the endoscope accessory further includes a substance trapping unit which is configured to trap a substance sucked through an inner hole of the insertion unit from the distal end region of the insertion unit in an area between the insertion unit and the connection unit.

6. The endoscope system according to claim 4, wherein a material of one part of the operation portion of the endoscope, which includes the entrance of the suction conduit, the entrance of the accessory insertion channel, and the communication path, is different from a material of the other part of the operation portion, and the material of the one part is more elastic than the material of the other part.

7. A method for mounting an endoscope accessory onto an endoscope, comprising:

providing an endoscope including:

an insertion portion which has one end region, an other end region, and an accessory insertion channel extending between the one end region and the other end region in the insertion portion and having an entrance in the other end region and an exit opened at the one end region, at least the one end region being configured to be inserted into a living organism, and an operation portion which is provided at the other end region of the insertion portion, in which a suction conduit is formed, the suction conduit having an entrance and an exit both of which are opened at different points in an outer surface of the operation portion, and the exit of the suction conduit being in communication with a suction device, the entrance of the suction conduit and the entrance of the accessory insertion channel in the outer surface being opened and disposed side by side, and wherein a communication path is formed in a region of the operation portion near to the entrances to communicate both of the suction conduit and the accessory insertion channel with each other;

providing an endoscope accessory including a tubular insertion unit which has a distal end region and a proximal end region, a tubular connection unit which is provided at the proximal end region of the tubular insertion unit, and a sealing unit which is provided on the tubular connection unit;

detachably inserting the distal end region of the tubular insertion unit of the endoscope accessory into the accessory insertion channel from the entrance of the accessory insertion channel in the operation portion of the endoscope and making the tubular insertion unit movable along the accessory insertion channel; and connecting the tubular connection unit of the endoscope accessory to the entrance of the suction conduit in the operation portion of the endoscope so as to be detachable and sealing a gap between the tubular connection unit and the entrance of the suction conduit while sealing a communication between the communication path and the suction conduit by the sealing unit of the connection unit, so that a suction force from the suction device through the suction conduit is supplied to the tubular insertion unit through the tubular connection unit.

8. The method for mounting an endoscope accessory onto an endoscope, according to claim 7, wherein a material of one part of the operation portion of the endoscope, which includes the entrance of the suction conduit, the entrance of the accessory insertion channel, and the communication path, is different from a material of the other part of the operation portion, and the material of the one part is more elastic than the material of the other part.

9. A method for mounting an endoscope accessory onto an endoscope, comprising:

providing an endoscope including:

an insertion portion which has one end region, an other end region, and an accessory insertion channel extending between the one end region and the other end region in the insertion portion and having an entrance in the other end region and an exit opened at the one end region, at least the one end region being configured to be inserted into a living organism, and an operation portion which is provided at the other end region of the insertion portion, in which a suction conduit is formed, the suction conduit having an entrance and an exit both of which are opened at different points in an outer surface of the operation portion, and the exit of the suction conduit being in communication with a suction device, the entrance of the suction conduit and the entrance of the accessory insertion channel in the outer surface are opened and disposed side by side, and wherein a communication path is formed in a region of the operation position near to the entrances to communicate both of the suction conduit and the accessory insertion channel with each other;

providing an endoscope accessory including a tubular insertion unit which has a distal end region and a proximal end region, a tubular connection unit which is provided at the proximal end region of the tubular insertion unit, a sealing unit which is provided on the tubular connection unit, and a substance trapping unit which is provided between the tubular insertion unit and the tubular connection unit and which is configured to trap a substance moved in an inner hole of the tubular insertion unit;

detachably inserting the distal end region of the tubular insertion unit of the endoscope accessory into the accessory insertion channel from the entrance of the accessory insertion channel in the operation portion of the endoscope and making the tubular insertion unit movable along the accessory insertion channel; and connecting the tubular connection unit of the endoscope accessory to the entrance of the suction conduit in the operation portion of the endoscope so as to be detachable and sealing a gap between the tubular connection unit and the entrance of the suction conduit while sealing a communication between the communication path and the suction conduit by the sealing unit of the connection unit, so that a suction force from the suction device through the suction conduit is supplied to the tubular insertion unit through the tubular connection unit.

10. The method for mounting an endoscope accessory onto an endoscope, according to claim 9, wherein a material of one part of the operation portion of the endoscope, which includes the entrance of the suction conduit, the entrance of the accessory insertion channel, and the communication path, is different from a material of the other part of the operation portion, and the material of the one part is more elastic than the material of the other part.

\* \* \* \* \*